United States Patent
Washburn et al.

(10) Patent No.: US 9,890,410 B2
(45) Date of Patent: *Feb. 13, 2018

(54) N-ACETYLHEXOSAMINE-CONTAINING N-GLYCANS IN GLYCOPROTEIN PRODUCTS

(71) Applicant: MOMENTA PHARMACEUTICALS, INC., Cambridge, MA (US)

(72) Inventors: Nathaniel Washburn, Littleton, MA (US); Enrique Arevalo, Dorchester, MA (US); Kevin Millea, Saugus, MA (US); Carlos J. Bosques, Arlington, MA (US); Jay Duffner, Shirley, MA (US); Brian Edward Collins, Arlington, MA (US)

(73) Assignee: MOMENTA PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,768

(22) Filed: Sep. 9, 2015

(65) Prior Publication Data
US 2016/0060675 A1   Mar. 3, 2016

Related U.S. Application Data

(63) Continuation of application No. 13/417,895, filed on Mar. 12, 2012, now Pat. No. 9,170,249.

(60) Provisional application No. 61/452,092, filed on Mar. 12, 2011.

(51) Int. Cl.
*G01N 31/00* (2006.01)
*G01N 33/53* (2006.01)
*C12P 21/00* (2006.01)
*G01N 33/15* (2006.01)
*C07K 16/00* (2006.01)

(52) U.S. Cl.
CPC ............ *C12P 21/005* (2013.01); *C07K 16/00* (2013.01); *G01N 33/15* (2013.01); *C07K 2317/41* (2013.01); *C07K 2317/52* (2013.01); *C07K 2317/524* (2013.01)

(58) Field of Classification Search
CPC ..... C12N 15/102; G01N 31/168; G01N 33/96
See application file for complete search history.

(56) References Cited

U.S. PATENT DOCUMENTS

| | | |
|---|---|---|
| 4,859,449 A | 8/1989 | Mattes |
| 5,047,335 A | 9/1991 | Paulson et al. |
| 5,068,190 A | 11/1991 | Horiuchi et al. |
| 5,234,905 A | 8/1993 | Kolhouse et al. |
| 5,340,453 A | 8/1994 | Jackson |
| 5,360,817 A | 11/1994 | von Izstein et al. |
| 5,370,872 A | 12/1994 | Cryz et al. |
| 5,411,942 A | 5/1995 | Widmer et al. |
| 5,456,909 A | 10/1995 | Marsh, Jr. et al. |
| 5,459,031 A | 10/1995 | Blumen et al. |
| 5,500,342 A | 3/1996 | Miyamura et al. |
| 5,510,261 A | 4/1996 | Goochee et al. |
| 5,554,730 A | 9/1996 | Woiszwillo et al. |
| 5,559,103 A | 9/1996 | Gaeta et al. |
| 5,567,684 A | 10/1996 | Ladisch et al. |
| 5,663,355 A | 9/1997 | Ganem et al. |
| 5,667,984 A | 9/1997 | Parekh et al. |
| 5,679,321 A | 10/1997 | Dasgupta et al. |
| 5,712,254 A | 1/1998 | Chaki et al. |
| 5,723,583 A | 3/1998 | Seed et al. |
| 5,753,454 A | 5/1998 | Lee |
| 5,759,823 A | 6/1998 | Wong et al. |
| 5,856,143 A | 1/1999 | Nilsson |
| 5,879,912 A | 3/1999 | Roth |
| 5,945,322 A | 8/1999 | Gotschlich |
| 6,030,815 A | 2/2000 | DeFrees et al. |
| 6,048,707 A | 4/2000 | Klock, Jr. |
| 6,096,555 A | 8/2000 | Hermentin et al. |
| 6,132,994 A | 10/2000 | Tawada et al. |
| 6,156,547 A | 12/2000 | Roth |
| 6,159,954 A | 12/2000 | Maruyama et al. |
| 6,190,522 B1 | 2/2001 | Haro |
| 6,218,149 B1 | 4/2001 | Morrison et al. |
| 6,261,805 B1 | 7/2001 | Wood |
| 6,274,568 B1 | 8/2001 | Schnaar et al. |
| 6,280,989 B1 | 8/2001 | Kapitonov et al. |
| 6,284,516 B1 | 9/2001 | Pollock et al. |
| 6,358,710 B1 | 3/2002 | Graves et al. |
| 6,597,996 B1 | 7/2003 | Venkataraman et al. |
| 8,034,906 B2 | 10/2011 | Borhani et al. |
| 9,170,249 B2 * | 10/2015 | Washburn ............... G01N 33/15 |
| 2002/0054878 A1 | 5/2002 | Lowman et al. |

(Continued)

FOREIGN PATENT DOCUMENTS

| | | |
|---|---|---|
| CN | 101001875 A | 7/2007 |
| CN | 101137757 A | 3/2008 |
| CN | 101681396 A | 3/2010 |
| JP | 2002-542787 A | 12/2002 |
| JP | 2005509403 A | 4/2005 |
| WO | 2000065070 A2 | 11/2000 |
| WO | 200180884 A1 | 11/2001 |
| WO | 200200879 A2 | 1/2002 |
| WO | 03/025133 A2 | 3/2003 |
| WO | WO-2004/050838 A2 | 6/2004 |
| WO | 2007011041 A1 | 1/2007 |
| WO | 2007087384 A2 | 8/2007 |
| WO | 2008063982 A2 | 5/2008 |
| WO | 2008128228 A1 | 10/2008 |
| WO | 2008128230 A1 | 10/2008 |
| WO | 2008130926 A2 | 10/2008 |
| WO | 2010136492 A2 | 12/2010 |
| WO | 2010138502 A2 | 12/2010 |
| WO | 2010141855 A1 | 12/2010 |
| WO | 2011127322 A1 | 10/2011 |
| WO | 2011127325 A1 | 10/2011 |
| WO | WO-2012/125553 A2 | 9/2012 |

OTHER PUBLICATIONS

Baker et al.(Biotechnology Engineering, vol. 73, No. 3, pp. 188-202).*

(Continued)

*Primary Examiner* — Lisa V Cook
(74) *Attorney, Agent, or Firm* — Brenda Herschbach Jarrell; Rolando Medina; Nishat A. Shaikh

(57) ABSTRACT

The present invention provides methods of evaluating a glycoprotein preparation for the absence, presence or amount of an N-acetylhexosamine glycan, e.g., an N-acetylglucosamine glycan.

34 Claims, 3 Drawing Sheets

(56) References Cited

U.S. PATENT DOCUMENTS

| | | | |
|---|---|---|---|
| 2003/0157108 | A1 | 8/2003 | Presta |
| 2003/0211573 | A1 | 11/2003 | Ryll |
| 2004/0077836 | A1 | 4/2004 | DeFrees et al. |
| 2004/0210396 | A1 | 10/2004 | Fischer et al. |
| 2006/0040353 | A1 | 2/2006 | Davidson et al. |
| 2006/0127950 | A1 | 6/2006 | Bosques et al. |
| 2006/0252672 | A1 | 11/2006 | Betenbaugh et al. |
| 2008/0261301 | A1 | 10/2008 | Kanda et al. |
| 2008/0280324 | A1 | 11/2008 | Rouwendal et al. |
| 2009/0041770 | A1 | 2/2009 | Chamberlain et al. |
| 2009/0069232 | A1 | 3/2009 | Callewaert et al. |
| 2009/0104603 | A1 | 4/2009 | Satomaa et al. |
| 2009/0203550 | A1 | 8/2009 | Venkataraman et al. |
| 2009/0226968 | A1 | 9/2009 | Betenbaugh et al. |
| 2009/0258014 | A1 | 10/2009 | Laterra et al. |
| 2009/0311732 | A1 | 12/2009 | Rossi et al. |
| 2009/0317834 | A1 | 12/2009 | Laine et al. |
| 2010/0048456 | A1 | 2/2010 | DeFrees et al. |
| 2010/0081150 | A1 | 4/2010 | Liu et al. |
| 2010/0113294 | A1 | 5/2010 | Venkataraman et al. |
| 2010/0129843 | A1 | 5/2010 | Parsons et al. |
| 2010/0144553 | A1 | 6/2010 | Bosques et al. |
| 2010/0173323 | A1 | 7/2010 | Strome et al. |
| 2011/0280873 | A1 | 11/2011 | Presta et al. |

OTHER PUBLICATIONS

Baker et al. (Biotechnology Engineering, vol. 73, No. 3, pp. 188-202).*

Roy Jefferis (Nature Biotechnology, vol. 24, No. 10, Oct. 2006, pp. 1230-1231).*

Roy Jefferis (Nature, vol. 8, Mar. 2009, pp. 226-234).*

Hirabayashi et al., "Separation technologies for glycomics", J. Chromatog. B Analyst. Biomed. Life Sci., May 2002, vol. 771, No. 1-2, pp. 67-87, Database Medline, US National Library of Medicine, Abstract.

Hodoniczky, et al., "Control of Recombinant Monoclonal Antibody Effector Functions by Fc N-Glycan Remodeling in Vitro" Biotechnol. Prog., 21:1644-1652 (2005).

Hoja-Lukowicz et al., "High-mannose-type oligosaccharides form human placental arylsulfatase A are core ficosylated as confirmed bu MALDI MS", Gyclobiology, vol. 10, No. 6, pp. 551-557 (2000).

Hosoi et al: "Modulation of Oligosaccharide Structure of a Pro-Urokinase Derivative (Pro-UKDELTAGS1) by Changing Culture Conditions of a Lymphoblastoid Cell Line Namalwa KJM-1 Adapted to Serum-Free Medium", Cytotechnology, Kluwer Academic Publishers, Dordrecht, NL, vol. 19, No. 2, pp. 125-135 (1996).

Hossler et al., "Systems analysis of N-glycan processing in mammalian cells" PLoS One, vol. 2(8)e713 pp. 1-17 (2007).

International Preliminary Report on Patenability including the Written Opinion from International Application Serial No. PCT/US2010/036058 dated Nov. 19, 2010.

International Preliminary Report on Patentability and Written Opinion for International application No. PCT/US2010/037454 dated Dec. 6, 2011.

International Preliminary Report on Patentability and Written Opinion from International Application Serial No. PCT/US2008/060365 dated Apr. 2, 2009.

International Preliminary Report on Patentability for International Application No. PCT/US2011/031637 dated Oct. 18, 2012.

International Preliminary Report on Patentability for International Application Serial No. PCT/US2012/028759 dated Jan. 14, 2014.

International Preliminary Report on Patentability from PCT Application Serial No. PCT/US2008/060354 dated Apr. 2, 2009.

International Preliminary Report on Patentability including the Written Opinion for International Application Serial No. PCT/US2011/031641 dated Aug. 17, 2011.

International Search Report and Written Opinion for corresponding International Application Serial No. PCT/US2011/31637 dated Aug. 30, 2011.

International Search Report and Written Opinion for corresponding International Application Serial No. PCT/US2013/043670 dated Jan. 7, 2014.

International Search Report and Written Opinion from International Serial No. PCT/US13/43696 dated Jan. 17, 2014.

International Search Report dated Jan. 7, 2014 in PCT/US2013/43671.

International Search Report for PCT/US2002/29285 filing date Dec. 23, 2002.

International Search Report for PCT/US2004/04423, dated Dec. 28, 2004.

International Search Report for PCT/US2010/36058, dated Nov. 19, 2010.

International Search Report for PCT/US2010/37454, dated Sep. 1, 2010.

International Search Report including the Written Opinion for International Application Serial No. PCT/US2011/031641 dated Aug. 17, 2011.

International Search Report including the Written Opinion for International Application Serial No. PCT/US2013/043667 dated Jan. 13, 2014.

International Search Report including Written Opinion for International Application Serial No. PCT/US13/43676 dated Jan. 16, 2014.

International Search Report including Written Opinion for International Application Serial No. PCT/US13/43693 dated Jan. 13, 2014.

International Search Report including Written Opinion for PCT/US13/43671 dated Jan. 7, 2014.

International Search Report including Written Opinion for PCT/US2012/28759 dated Sep. 4, 2012.

International Search Report including Written Opinion for PCT/US2013/43674 dated Jan. 15, 2014.

International Search Report including Written Opinion for PCT/US2013/43675 dated Dec. 23, 2013.

Jabs et al. Fast and Extensive Mass Spectrometry Characterization of Theraputic mABs: The Panitumumab Case Study [online] CASSS Mass Spec Meeting Sep. 14, 2012 Poster 125 [ retrieved Dec. 10, 2013].

Jefferis, "Glycosylatin of Human IgG Antibodies: Relevance to Therapeutic Applications" Biopharm. Advanstar Communications, Inc., 14(9):19-27 (2001).

Jong Hyun Nam et al: "The effects of culture conditions on the glycosylation of secreted human placental alkaline phosphatase produced in Chinese hamster ovary cells", Biotechnology and Bioengineering, vol. 100, No. 6, 4, pp. 1178-1192 (2008).

Kakehi et al., "Analysis of glycoproteins, glycopeptides and glycoprotein-derived polysaccharides by high-performance capillary electrophoresis", J. Chromatogr. A., 1996, vol. 720, No. 1-2, pp. 377-393.

Kanda et al., "Comparison of biological activity among nonfucosylated therapeutic IgF1 antibodies with three different N-linked Fc oligosaccharides: the high-mannose, hybride, and complex types" Glycobiology, vol. 17(1) pp. 104-118 (2007).

Kanda et al., "Establishment of a GDP-mannose 4,6-dehydratase (GMD) knockout host cell line: A new strategy for generating completely non-cucosylated recombinant therapeutics" Journal of Biotechnology, vol. 130 pp. 300-310 (2007).

Kawashima et al., "Tyrosine kinase activity of epidermal growth factor receptor is regulated by GM3 binding through carbohydrate to carbohydrate interactions" J. Biol. Chem. vol. 284(10) pp. 6147-6155 (2009).

Keiser et al., "Direct isolation and sequencing of specific protein-binding glycosaminoglycans", Nature Medicine, 2001, vol. 7, No. 1, pp. 123-128.

Keppler et al., "Biosynthetic modulation of sialic acid-dependent virus-receptor interactions of two primate polyoma viruses", J. Biol. Chem., 1995, vol. 270, No. 3, pp. 1308-1314.

Kim et al., "Production and N-glycan analysis of secreted human erythropoietin glycoprotein in stably transfected *Drosophilia* S2 cells", Biotechnol. and Bioeng., 2005, vol. 92, No. 4, pp. 452-461.

Kosa et al., "Modification of cell surfaces by enzymatic introduction of special sialic acid analogues", Biochm. Biophys. Res. Commun., 1993, vol. 190, pp. 914.

(56) References Cited

OTHER PUBLICATIONS

Krapp et al., "Structural Analysis of Human IgG-Fc Glycoforms Reveals a Correlation Between Glycosylation and Structural Integrity", Journal of Molecular Biology, 325(5) pp. 979-989 (2003).

Kunkel et al., "Comparisons of the glycosylation of a monoclonal antibody produced under nominally identical cell culture conditions in two different bioreactors", Biotechnol. Prog., 2000, vol. 16, pp. 462-470.

Kunkel et al., "Dissolved oxygen concentration in serum-free continuous culture affects N-linked glycosylation of a monoclonal antibody", Journal of Biotechnology, 1998, vol. 62, pp. 55-71.

Le Floch et al., "HPCE monitoring of the N-glycosylation pattern and sialylation of murine erythropoietin produced by CHO cells in batch processes", Biotechnol. Prog., 2004, vol. 20, pp. 864-871.

Lee et al, "A mutation causing a reduced level of expression of six beta4-galactosyltransferase genes in the basis of the Lec19 CHO glycosylation mutant." Biochemistry (2003) vol. 42 No. 42 pp. 12349-12357.

Lifely M R et al: "Glycosylation and biological-activity of CAMPATH-1H expressed in different cell-lines and grown under different culture conditions", Glycobiology, Oxford University Press, US, vol. 5, No. 8, pp. 813-822 (1995).

Lin et al., "Unusual stereoselectivity in sialic acid aldolase-catalyzed aldol condensations: synthesis of both enantiomers of high-carbon monosaccharides", J. Am. Chem. Soc., 1992, vol. 114, pp. 10138-10145.

Lipscomb et al., "Effect of production method and gene amplification on the glycosylation pattern of a secreted reporter protein in CHO cells", Biotechnol. Prog., 2005, vol. 21, pp. 40-49.

Live et al., "Conformational influences of a glycosylation of a peptide: a possible model for the effect of glycsylation on the rate of protein folding", Proceedings of the National Academy of Sciences of the United States of America, 1996, vol. 93, No. 23, pp. 12759-12761, XP002293395 ISSN: 0027-8424.

Lopez-Avalos et al., "The UDPase activity of the Kluyveromyces lactis Golgi GDPase has a riole in uridine nucleotide sugar transport into Golgi vesicles", Glycobiology, vol. 11(5) pp. 413-422 (2001).

Lucocq, et al., "Detection of Terminal N-Linked N-acetylglucosamine Residues in the Golgi Apparatus using Galactosyltransferase and Endoglucosaminidase F/Peptide N-glycosidase F: Adaptation of a Biomedical Approach to Electron Microscopy" The Journal of Histochemistry and Cytochemistry, 35(1):67-74 (1987).

MacMillan et al.,"Selective in vitro glycosylation of recombinant proteins: semi-synthesis of novel homogeneous glycoforms of human erythropoietin", Chemistry and Biology, 2001, vol. 8, pp. 133-145.

Millward et al., "Effect of constant and variable domain glycosylation on pharmacokinetics of therapeutic antibodies in mice" Biologicals, 36, pp. 41-47 (2008).

Moran et al., "A systematic approach to the validation of process control parameters for monoclonal antibody production in fed-batch culture of a murine myeloma", Biotechnol. and Bioeng., 2000, vol. 69, No. 3, pp. 242-255.

Mueller et al., "Recombinant glycoprotein product quality in proliferation-controlled BHK-21 cells", Biotechnol. and Bioeng., 1999, vol. 65, No. 5, pp. 529-536.

Nairn et al., "Regulation of glycan structures in animal tissues: transcript profiling of glycan-related genes" J. Biol. Chem., vol. 282(25) pp. 17298-17313 (2008).

Nyberg et al ., "Metabolic effects on recombinant interferon-g glycosylation in continuous culture of Chinese hamster ovary cells", Biotechnol. and Bioeng., 1999, vol. 62, No. 3.

Oh et al.,"Effect of N-acetylcystein on butyrate-treated Chinese hamster overy cells to improve the production of recombinant human interferon-b-1a", Biotechnol. Prog., 2005, vol. 21, pp. 1154-1164.

Pace et al., "Characterization of Minor N-linked Glycans on Antibodies Using Endo H Release and MALDI-Mass Spectrometry" Analytical Letters, vol. 42, No. 11, pp. 1711-1724 (2009).

Park et al., "Expression of carbamoyl phosphate synthetase I and ornithine transcarbamoylase genes in Chinese hamster ovary dhfr- cells decreases accumulation of ammonium ion in culture media", Journal of Biotechnology, 2000, vol. 81, pp. 129-140.

Plante et al., "Automated solid-phase synthesis of oligosaccharides", Science, 2001, vol. 291, No. 5508, pp. 1523-1527.

Plante et al., "Formation of b-glucosamine and b-mannose linkages using glycosyl phosphates", Org. Lett., 2000, vol. 2, No. 24, pp. 3841-3843.

Rao et al., "Influence of Glycopeptide Structure on the Regulation of Galactosyltransferase Activity" Biochemistry (1978) vol. 17 No. 26 pp. 5632-5638.

Reitman et al., "Mouse Lymphoma Cell Lines Resistant to Pea Letin are defective in Fucose Metabolism", J Biol Chem., vol. 255(20) pp. 9900-9906 (1980).

Restelli et al., "The effect of dissolved oxygen on the production and the glycosylation profile of recombinant human erythropoietin produced from CHO cells", Biotechnology and Bioengineering, 2006, vol. 94, No. 3, pp. 481-494.

Ripka et al., "Two Chinese Hamster Ovary Glycosylation Mutants Affected in the Converstion of GOP-Mannose to GOP-Fucose" Arch Biochem Biophys vol. 249(2) pp. 533-545 (1986).

Ritzenthaler et al., "Reevaluation of the effets of brefeldin A on plant cells using tobacco Bright Yellow 2 cells expressing Golgi-targeted green fluoresent protein and COPI antisera" Plant Cell, vol. 14(1) pp. 237-261 (2002).

Robinson D K et al: "Characterization of a recombinant antibody produced in the course of a high yield fed-batch process", Biotechnology and Bioengineering, Wiley & Sons, Hoboken, NJ, US, vol. 44, No. 6, 5, pp. 727-735 (1994).

Rodriguez J et al: "Enhanced production of monomeric interferon-[beta] by CHO cells through the control of culture conditions", Biotechnology Progress, American Institute of Chemical Engineers, US, vol. 21, No. 1, pp. 22-30 (2005).

Santell et al., "Aberrant metabolic sialylation of recombinant proteins expressed in Chinese hamster ovary cells in high productivity cultures", Biochemical and Biophysical Research Communications, 1999, vol. 258, pp. 132-137.

Sasaki et al.,"Site-specific glycosylation of human recombinant erythropoietin: analysis of glycopeptides of peptides at each glycosylation site by fast atom bombardment mass spectrometry", Biochemistry, 1988, vol. 27, pp. 8618-8626.

Schulz et al., "Mediators of galactose sensitivity in UDP=galactoe 4'-epimerase-impaired mammalian cells" J. Biol Chem, 280 (14) pp. 13493-13502 (2005).

Schuster et al., "Improved effector functions of a therapeutic monoclonal Lewis V-specific antibody by glycoform engineering", Cancer Res., 2005, vol. 65, No. 17, pp. 7934-7941.

Search Report from Chinese Application No. 201180022319.9 dated Sep. 30, 2102.

Senger et al., "Effect of shear stress on intrinsic CHO culture state and glycosylation of recombinant tissue-type plasminogen activator protein", Biotechnol. Prog., 2003, vol. 19, pp. 1199-1209.

Serrato et al., "Heterogeneous conditions in dissolved oxygen affect N-glycosylation but not productivity of a monoclonal anitbody in hybridoma cultures", Biotechnology and Bioengineering, 2004, vol. 88, No. 2, pp. 176-188.

Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives", Glycobiology, 1991, vol. 1, pp. 187-191.

Sherman, MD, RE, Biosimilar Biological Products. Biosimilar Guidance Webinar. US Food and Drug Administration pp. 1-22 (2012).

Shields et al., "Lack of Fucose on Human IgG1 N-Linked Oligosaccharide Improves Binding to Human FcyRIII and Antibody-dependent Cellular Toxicity," The Journal of Biological Chemistry, 277(30):26733-236740(2002).

Shinkawa et al., The absense of fucose but not the presence of galactose or bisecting N-acetylglucosamine of human IgG1 com-

(56) References Cited

OTHER PUBLICATIONS plex-type oligosaccharides shows the critical role of enhancing antibody-dependent cellular cytotoxicity. J Biol Chem., vol. 278(5) pp. 3466-3473 (2003).
Sokolowski et al., "Conformational analysis of biantennary glycans and molecular moldeling of their complexes with lentil lectin", Journal of Molecular Graphics and Modeling, Feb. 1997, vol. 15, No. 1, pp. 37-42, 54, XP002293396 ISSN: 1093-3263.
Sparks et al., "Synthesis of potential inhibitors of hemagglutination by Influenza virus: chemoenzymic preparation of N-5 analogs of N-acetylneuraminic acid", Tetrahedron, 1993, vol. 49, pp. 1.
Spearman et al., "Production and glycosylation of recombinant â-interferon in suspension and cytopore microcamer cultures of CHO cells", Biotechnol. Prog., 2005, vol. 21, pp. 31-39.
Srinivas et al., "Pharmacokinetics and Pharmacodynamics of CTLA4Ig (BMS-188667), a Novel Immunosuppressive Agent, in Monkeys following Multiple Doses" Journal of Pharmaceutical Sciences, 85(1) pp. 1-4 (1996).
Srinivas et al., "Assessment of Dose Proportionality, Absolute Bioavailability, and Immunogenicity Response of CTLA4Ig (BMS-188667), a Novel Immunosuppressive Agent, Following Subcutaneous and Intravenous Administration to Rats" Pharmaceutical Research, 14(7) pp. 911-916 (1997).
Sung et al., "Effect of sodium butyrate on the production, heterogeneity and biological activity of human thrombopoietin by recombinant Chinese hamster ovary cells", Journal of Biotechnology, 2004, vol. 112, pp. 232-335.
Supplemental Partial European Search Report from 10781083.0 dated Nov. 27, 2015.
Supplemental Partial European Search Report, dated Aug. 31, 2004 for Application No. 02773390.6.
Supplemental Partial European Search Report, dated Jan. 23, 2015 for Application No. EP 12757887.0.
Takeuchi et al.,"Structures and functional roles of the sugar chains of human erythropoietins", Glycobiology, 1991, vol. 1, No. 4, pp. 337-346.
Tran et al., "Separation of carbohydrate-mediated microheterogeneity of recombinant human erythropoietin by free solution capillary electrophoresis", Journal of Chromatography, 1991, vol. 542, pp. 459-471.
Trombetta et al., "Glycoprotein reglucosylation and nucleotide sugar utlization in the secretory pathway: identification of a nucleoside diphosphatase in the endoplasmic reticulum" The EMBO Journal, vol. 18, No. 12, pp. 3282-3292 (1999).
Trummer et al., "Process parameter shifting: part I. Effect of DOT, pH, and temperature on the performance of Epo-Fc expressing CHO cells cultivated in controlled batch bioreactors", Biotechnol. and Bioeng., 2006, vol. 94, No. 6, pp. 1033-1044.
Umaña et al., "Engineered glycoforms of an antineuroblastoma IgG1 with optimized antibody-dependent cellular cytotoxic activity", Nature Biotechnology, 1999, vol. 17, pp. 176-180.
Van Berkel et al., "N-linked glycosylation is an important parameter for optimal selection of cell lines producing biopharmaceutical human IgG", Biotechnology Progress, Vo;. 25, No. 1, pp. 244-251 (2009).
Van De Nieuwenhof et al., "Recombinant glycodelin carring the same type of glycan structures as contraceptive glycodelin-A can be produced in human kidney 293 cells but not in Chinese hamster ovary cells" Eur. J. Biochem, vol. 267 pp. 4753-4762 (2000).
Varki, "Radioactive tracer techniques in the sequencing of glycoprotein oligosaccharides", J. FASEB, 1991, vol. 2, p. 226-235.
Venkataraman et al., "Sequencing complex polysaccharides", Science, 1999, vol. 286, pp. 537-542.
Von Der Lieth, "Expanding proteomics to glycobiology: biocomputing approaches understanding the function of sugar", Pacific Symposium on Biocomputing, 2002, Abstract.
Von Horsten, et al., "Production of non-fucosylated antibodies by co-expression of heterologous GDP-6-deoxy-D-lyxo-4-hexulose reductase" Glycobiology, 20(12):1607-1618 (2010).

Wang et al., "EDEM an ER quality control receptor" Nat. Struct. Biol., vol. 10(5) pp. 319-321 (2003).
Akiyama et al., "Analysis of the role of glycosylation of the human fibronectin receptor", J. Biol. Chem. vol. 264(30) pp. 18011-18018 (1989).
Andersen et al., "Multiple cell culture factors can affect the glycosylation of Asn-184 in CHO-produced tissue-type plasminogen activator", Biotechnol. Bioeng., 2000, vol. 70, pp. 25-31.
Andrade et al., "Solid-phase oligosaccharide synthesis: preparation of comlex structures using a novel linker and different glycosylating agents", Org. Lett., 1999, vol. 1, No. 11, pp. 1811-1814.
Anumula et al., "Advances in fluorescence derivatization methods for high-performance liquid chromatographic analysis of glycoprotein carbohydrates", Analytical Biochemistry, 305(1), pp. 1-23 (2006).
Baker et al., "Metabolic control of recombinant protein N-glycan processing in NSO and CHO cells", Biotechnol. Bioeng., 2001, vol. 73, pp. 188-202.
Becker et al., "Fucose: biosynthesis and biological function in mammels" Glycobiology, Jul. 13(7) pp. 41R-53R (2003).
Bohne et al., "Sweet—WWW-based rapid 3D construction of oligo- and polysaccharides", Bioinformatics, Sep. 1999, vol. 15, No. 9, pp. 767-768, XP 001024942 ISSN: 1367-4803, Oxford University Press, Surrey, GB.
Bollati-Foglin et al., "Temperature reduction in cultures of hGM-CSF-expressing CHO cells: effect on productivity and product quality", Biotechnol. Prog., 2005, vol. 21, pp. 17-21.
Bowman et al., "Biosynthesis of L-selectin ligands: sulfation of sialyl Lewis x-related oligosaccharides by a family of GlcNac-6-sulfotransferases", Biochemistry, 2001, vol. 40, No. 18, pp. 5382-5391.
Breidenbach et al., "Targeted metabolic labeling of yeast N-glycans with unnatural sugars" Proc. Natl. Acad. Sci., vol. 107(9) pp. 3988-3993 (2010).
Broschat et al., "Purification and characterization of GDP-D-mannose 4,6-dehydratase from porcine", Thyroid. Eur. J. Biochem., 1985, vol. 153, No. 2, pp. 397-401.
C.E. Joosten et al: "Effect of Culture Conditions on the Degree of Sialylation of a Recombinant Glycoprotein Expressed in Insect Cells", Biotechnology Progress, vol. 19, No. 3, 6 pp. 739-749 (2003).
Cabrera et al., "Influence of culture conditions of the N-glycosylation of a monoclonal antibody specific for recombinant hepatitis B surface antigen", Biotechnol. Appl. Biochem., 2005, vol. 41, pp. 67-76.
Chen et al., "Independent Lec1A CHO Glycosylation Mutants Arise from Point Mutations in N-Acetylglucosaminyltransferase I that Reduce Affinity for Both Substrates. Molecular Consequences Based on the Crystal Structure of GlcNac-TI", Biochemistry vol. 40(30) pp. 8765-8772 (2001).
Chen et al., "T cell receptors signaling co-regulates multiple Golgi genes to enhance N-glycan branching" J. Boil. Chem. vol. 284(47) pp. 32454-32461 (2009).
Chen P et al: "Effects of elevated ammonium on glycosylation gene expression in CHO cells", Metabolic Engineering, Academic Press, US, vol. 8, No. 2, pp. 123-132 (2006).
Clark et al., "Gene-expression profiles for five key glycosylation genes for galactose-fed CHO cells expression recombinant IL-4/13 cytokine trap", Biotechnol. and Bioeng., 2005, vol. 90, No. 5, pp. 568-577.
Cooper et al., "GlycoSuiteDB: a curated relational database of glycoprotein glycan structures and their biological sources. 2003 update", Nucleic Acids Research, 2003, vol. 31, No. 1, pp. 511-513.
Cooper et al., "GlycoSuiteDB: a new curated relational database of glycoprotein glycan structures and their biological sources", Nucleic Acids Research, 2001, vol. 29, No. 1, pp. 332-335.
Cornil et al. Tumor cell surface beta 1-4-linked galactose binds to lectin(s) on microvascular endothelial cells and contributes to organ colonization. J Cell Biol. Aug. 1990;111 (2):773-81.

(56) References Cited

OTHER PUBLICATIONS

Cox et al: "Glycan Optimization of a Human Monoclonal Antibody in the Aquatic Plant Lemna Minor", Nature Biotechnology, Nature Publishing Group, New York, NY, US, vol. 24, No. 12, pp. 1591-1597 (2006).
Crowell et al., "Amino acid and manganese supplementation modulates the glycosylation state of erythropoietin in a CHO culture system", Biotechnol. and Bioeng., 2006, pp. 538-549.
Debray et al, "Glycoprotein Analysis: General Methods", In: "Encyclodpedia of Analytical Chemistry" pp. 1-39.
Donaldson et al., "The use of lectins to select subpopulations of insect cells", Biotechnol. and Bioeng., 1999, vol. 61, pp. 616-619.
Dorka et al., "Modelliong Batch and Fed-Batch Mammalian Cell Cultures for Optimizing MAb Productivity", M.S. Thesis pp. 1-197 (2007).
Drecktrah et al., "Inhibition of a Golgi complex lysophospholipid acyltransferase induces membrane tuble formation and retrograde trafficing" Mol. Biol. Cell, vol. 14(8) pp. 3459-3469 (2003).
European Patent Office, Communication pursuant to Article 96(2) dated Oct. 30, 2007 in related European Patent Application No. 02 773 390.6.
Extended European Search Report dated Mar. 1, 2013.
Extended European Search Report from European Application No. 11766759.2 dated Aug. 19, 2013.
Extended European Search Report from European application serial No. 11766762.6 dated Jan. 28, 2014.
Extended European Search Report from European Patent Application No. 12757887.0 dated May 28, 2015.
Fareed, "S-9-10 synthetic and biotechnology derived glycomimetics", Impact on Drug Development, 2000, Database Google 6th Annual Pg Forum, Abstract.
FDA. Scientific Considerations in Demonstrating Biosimilarity to a Reference Product [online] Feb. 2012 [retrieved Dec. 10, 2013].
Ferrara et al., "Modulation of therapeutic antibody effector functions by glycosylation engineering: influence of golgi enzyme localization domain and co-expression of heterologous b 1, 4-N-acetylglucosaminyltransferase III and golgi a-mannosidase II", Biotechnol. and Bioeng., 2006, vol. 93, No. 5, pp. 851-861.
Fitz et al., "Combined use of subtilisin and N-acetyl neuraminic acid aldolase for the synthesis of a fluorescent sialic acid", J. Org. Chem., 1994, vol. 59, pp. 8279.
Fleischer Eta L., "Mechanism of Glycosylation ion the Golgi Apparatus" The Journal of Histochemistry and Cytochemistry, vol. 31, No. 8, pp. 1033-1040 (1983).
Forno et al., "N- and O-linked carbohydrates and glycosylation site occupancy in recombinant human granulocytemacrophage colony-stimulating factor secreted by a Chinese hamster overy cell line", Eur. J. Biochem., 2004, vol. 271, pp. 907-919.
Freeze et al., "Use of Glycosidases to Study protein trafficking" Curr Protoc Cell Bio. (15.2.1-15.2.26) (1999).
Fukuda et al., "Survival of recombinant erythropoietin in the circulation: the role of carbohydrates", Blood, 1989, vol. 73, pp. 84-89.
Gates et al., "Glycoprotein analysis manual" internet citation, pp. 1-89, retrieved from the Internet:URL:download. bioon.com.cn/view/upload/201301/27194411__2997.pdf.
Gawlitzek et al., "Ammonium alters N-glycan structures of recombinant TNFR-IgG: degradative versus biosynthetic mechanisms", Biotechnol. and Bioeng., 2000, vol. 68, No. 6, pp. 637-646.
Gawlitzek et al., "Characterization of changes in the glycosylation pattern of recombinant proteins from BHK-21 cells due to different culture conditions", Journal of Biotechnology, 1995, vol. 42, pp. 117-131.
Goldman et al., "Monitoring recombinant human interferon-g N-glycosylation and during perfused fluidized-bed and stirred-tank batch culture of CHO cells", Biotechnol. and Bioeng., 1998, vol. 60, pp. 596-607.
Gu et al., "Improvement of interferon-g sialylation in Chinese hamster ovary cell culture by feeding of N-acetylmannosamine", Biotechnol. and Bioeng., 1998, vol. 58, pp. 642-648.

Hamid et al., "A strategy to reveal potential glycan markers from serum glycoproteins associated with breast cancer progression" Glycobiology (2008) vol. 18 No. 12 pp. 1105-1118.
Hara et al., "Determination of Mono-O-acetylated N-Acetylneuraminic Acids in Human and Rat Sera by Fluorometric High-Performance Liquid Chromatography" Analytical Biochemistry, 179 pp. 162-166 (1989).
Harue Imai-Nishiya et al., "Double knockdown of a 1,6 fucosyltransferase (FUT8) and GDP-mannose 4,6-dehydratase (GMD) in antibody-producing cells: a new strategy for generating fully non-fucosylated therapeutic antibodies with enhanced ADCC", BMC Biotechnology, 2007, vol. 7, No. 84, pp. 1-13.
Hendrick V et al: "Increased productivity of recombinant tissular plasminogen activator (t-PA) by butyrate and shift of temperature: a cell cycle phases analysis", Cytotechnology, Kluwer Academic Publishers, DO, vol. 36, No. 1-3, pp. 71-83 (2001).
Hewitt et al., "Solution and solid-support synthesis of a potential leishmaniasis carbohydrate vaccine", J. Org. Chem., 2001, vol. 15, No. 66(12), pp. 4233-4243.
Hills et al., "Metabolic control of recombinant monoclonal antibody N-glycosylation in GS-NSO cells", Biotechnol. and Bioeng., 2001, vol. 75, pp. 239-251.
Watson et al.,"Capillary electrophoresis separation of human recombinant erythropoietin (r-HuEPO) glycoforms", Analytical Biochemistry, 1993, vol. 210, pp. 389-393.
Watson et al.,"Structure determination of the intact major sialylated oligosaccharide chains of recombinant human erythropoietin expressed in Chinese hamster overy cells", Glycobiology, 1994, vol. 4, No. 2, pp. 227-237.
Webb J W et al., Structural characterization of intact, branched oligosaccharides by high performance liquid chromatography and liquid secondary ion mass spectrometry Analytical Biochemistry, vol. 169, pp. 337-349 (1998).
Weiner et al., "A senstive enzyme immunoassay for the quantitation of human CTLA4Ig fusion proten in mouse serum: pharmacokinetic application to optimizing cell line selection" Journal of Pharmaceutical and Biomedical Analysis, 15(5) pp. 571-579 (1997).
Wong et al., "Impact of dynamic online fed-batch strategies on metabolism, productivity and N-glycosylation quality in CHO cell cultures", Biotechnol. and Bioeng., 2005, vol. 89, No. 2, pp. 164-177.
Wopereis et al., "Mechanisms in Protein O-Glycan Biosynthesis and Clinical and Molecular Aspects of Protein O-Glycan Biosynthesis Defects: A Review" Clinical Chem., vol. 52(4) pp. 547-600 (2006).
Wright et al., "In vivo trafficking and catabolism of IgG1 antibodies with Fc associated carbohydrates of differing structure", Glycobiology, 2000, vol. 10, No. 12, pp. 1347-1355.
Wuhrer et al., "Glycosylation profiling of immunoglobulin G (IgG) subclasses from human serum" Proteomics (2007) vol. 7 No. 22 pp. 4070-4081.
Yang et al. "Bio-Basis Function Neural Network for Prediction of Protease Cleavage Sites in Proteins" IEEE Transactions on Neural Netwroks, vol. 16, pp. 263-274 (2005).
Yang et al., "Achievement of high cell density and high antibody productivity by a controlled-fed perfusion bioreactor process", Biotechnol. and Bioeng., 2000, vol. 69, No. 1, pp. 74-82.
Yang et al., "Effect of ammonia on the glycosylation of human recombinant erythropoietin in culture", Biotechnol. Prog., 2000, vol. 16, pp. 751-759.
Ye et al., "N-glycan branching requirement in neuronal and postnatal viability", Glycobiology, vol. 14(6) pp. 547-558 (2004).
Yoko-O, et al., "An N-acetylglucosaminyltransferase of the Golgi apparatus of the yeast Saccharomyces cerevisiae that can modify N-linked glycans" Glycobiology, 13(8):581-589 (2003).
Yoon et al., "Effect of culture pH on erythropoietin production by Chinese hamster overy cells grown in suspension at 32.5 and 37 degree Celsius", Biotechnol. and Bioeng., 2005, vol. 89, No. 3, pp. 345-356.
Yoon et al., "Effect of simultaneous application of stressful culture conditions on specific productivity and heterogeneity of erythropoietin in Chinese hamster overy cells", Biotechnol. Prog., 2004, vol. 20, pp. 1293-1296.

(56) References Cited

OTHER PUBLICATIONS

Yuen et al., "Relationships between the N-glycan structures and biological activities of recombinant human erythropoietins produced using different culture conditions and purification procedures", British Journal of Haematology, 2003, vol. 121, pp. 511-526.

Yuk et al., "Changes in the overall extent of protein glycosylation by Chinese hamster overy cells over the course of batch culture", Biotechnol. Appl. Biochem., 2002, vol. 36, pp. 133-140.

Yuk et al., "Glycosylation by Chinese hamster overy cells in dolichol phosphate-supplemented cultures", Biotechnol. Appl. Biochem., 2002, vol. 36, pp. 141-147.

Zhang et al., "Quantitative analysis and process monitoring of site-specific glycosylation microheterogeneity in recombinant human interferon-gamma from Chinese hamster ovary cell culture by hydrophilic interaction chromatography" Journal of Chromatography B: Biomedical Sciences & Applications, vol. 712, No. 1-2, pp. 73-82 (1998).

\* cited by examiner

N-ACETYLHEXOSAMINE-CONTAINING N-GLYCANS IN GLYCOPROTEIN PRODUCTS

This application is a continuation of U.S. Ser. No. 13/417,895, filed Nov. 26, 2012, now U.S. Pat. No. 9,170,249, which claims priority under USC § 119(e) to U.S. Provisional Patent Application Ser. No. 61/452,092, filed on Mar. 12, 2011, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on Jul. 7, 2014, is named M2050-706410_SL.txt and is 719 bytes in size.

FIELD OF THE INVENTION

The present invention relates to methods and materials for the detection of particular glycan structures in glycoproteins.

BACKGROUND OF THE INVENTION

Antibodies represent a growing class of biotherapeutic drugs in the pharmaceutical market and in development for a variety of indications. Unlike a small molecules, biologics are actually a mixture of isoforms all of which are contain the same peptide backbone, but differ in modifications and which may have a range of pharmacokinetic, pharmacodymanic or safety profiles. It is therefore important to routinely monitor product quality. Antibodies are glycoproteins which contain at least one variably occupied N-glycosylation site. N-glycosylation in antibody therapeutics is thought to influence pharmacokinetics and structural integrity of the molecule (Krapp, Mimura et al. 2003).

SUMMARY OF THE INVENTION

The present invention is based, in part, on the discovery of an N-acetylhexosamine glycan structure that can be present on glycoproteins, e.g., a glycosylated antibody. In some embodiments, the presence or amount of the N-acetylhexosamine is associated with a particular production parameter or parameters. The absence, presence and/or amount of this glycan structure can be used, inter alia, for evaluating or processing a glycoprotein preparation, e.g., to determine whether to accept or reject a batch of a glycoprotein, e.g., a glycosylated antibody, or to guide or control a production parameter or parameters used to produce a glycoprotein, e.g., a glycosylated antibody. In some embodiments, the absence, presence or amount of this structure in a glycoprotein composition can be compared, e.g., to a reference standard, e.g., to make a decision regarding the glycoprotein preparation, e.g., a decision to classify, select, accept or discard, release or withhold, process into a drug product, ship, move to a different location, formulate, label, package, release into commerce, or sell or offer for sale the glycoprotein, e.g., a glycosylated antibody. In other embodiments, the decision can be to accept, modify or reject a production parameter or parameters used to make the glycoprotein, e.g., a glycosylated antibody.

Thus, in a first aspect, the disclosure features methods for evaluating a glycoprotein preparation. In some embodiments, the method includes:

providing one or more preparations of a glycoprotein, e.g., a glycosylated antibody preparation; and
determining, e.g., using a separation method, the absence, presence and/or amount of an N-acetylhexosamine glycan associated with the glycoprotein.

The determining step may include one or more of the following: (a) isolating a glycoprotein produced by a cell and determining if an N-acetylhexosamine glycan is present on the glycoprotein, (b) isolating a glycoprotein preparation produced by a cell and determining the presence or amount of the N-acetylhexosamine on glycoproteins of the preparation, (c) isolating glycans from a glycoprotein produced by a cell and determining if the glycans of the glycoprotein include an N-acetylhexosamine glycan, and (d) providing at least one peptide from a glycoprotein produced by cell, and determining the presence glycans containing an N-acetylhexosamine on the at least one peptide. The technique used to measure the N-acetylhexosamine can include one or more of the following methods, and combinations of any of these methods: chromatographic methods, mass spectrometry (MS) methods, electrophoretic methods (such as capillary electrophoresis), nuclear magnetic resonance (NMR) methods, monosaccharide analysis, fluorescence methods, UV-VIS absorbance, enzymatic methods, and use of a detection molecule (such as an antibody or lectin).

The source of glycans can be selected from the group consisting of: a population of cells, e.g., CHO cells; an isolated glycoprotein, e.g., an isolated glycosylated antibody; peptides derived from the cleavage of a glycoprotein, e.g., a glycosylated antibody; or glycans derived from the glycoprotein. In some embodiments, the method includes treating a source of glycans or glycopeptides with one or more enzymes, e.g., PNGase, followed by analysis of the glycan population. In some embodiments this method includes treating the glycopeptides with a chemical to release the glycan, e.g. acid hydrolysis, followed by analysis of the released glycans or monosaccharides and or analysis of the glycan attached to a single amino acid.

In some embodiments, the method used provides a quantitative measure of an N-acetylhexosamine glycan. In some embodiments, the method used provides a qualitative measure.

In some embodiments, the method also includes preparing a glycoprotein preparation, cleaving one or more glycans from the glycoprotein preparation (e.g., with one or more enzyme such as PNGase, and determining the absence, presence or amount of an N-acetylhexosamine glycan.

In certain embodiments, the method is conducted during a production run for a therapeutic glycoprotein by obtaining a sample from the cell culture of the production line, e.g., to monitor glycan structure during production. In certain embodiments, the determining step is repeated at least once over time, e.g., the determining step is repeated at least once, twice, three times or more, during the time period of culture of the cells. In some embodiments, the method is conducted during the storage of a glycoprotein by obtaining a sample from the glycoprotein composition, e.g., to monitor glycan structure stability during storage. In certain embodiments, the determining step is repeated at least once over time, e.g., the determining step is repeated at least once, twice, three times or more, during the storage of the glycoprotein composition. In other embodiments, the method is conducted on a glycoprotein composition, e.g., as part of a quality or release testing of the glycoprotein composition.

In some embodiments, the determining step includes comparing the level of N-acetylhexosamine glycan containing glycoproteins in a first glycoprotein preparation produced from a first population of cells, e.g., produced under a first production parameter or parameters, to the level of N-acetylhexosamine glycan containing glycoprotein in a second glycoprotein preparation produced from a second population of cells and/or the same cells under a different production parameter or parameters. In some such embodiments, the presence or amount of an N-acetylhexosamine glycan of a glycoprotein preparation is determined and compared to the presence or amount of the N-acetylhexosamine glycan of a glycoprotein produced under a different production parameter or parameters.

In some embodiments, the method comprise a step of comparing the level of N-acetylhexosamine glycans to a reference standard (e.g., to a control level, or to a range or value in a product specification).

In certain embodiments of the method, the determining step includes use of a detection molecule which is able to detect the presence or absence of an N-acetylhexosamine glycan. In certain embodiments, the detection molecule comprises an antibody that is able to bind to N-acetylhexosamine. In some embodiments, the detection molecule may comprise a fluorescent moiety, or a radioisotope moiety. In some embodiments this comprises another sugar that forms a covalent linkage to the N-acetylhexosamine. In some embodiments, the detection molecule may comprise a fluorescent moiety, or a radioisotope moiety. In some embodiments this comprises another sugar that forms a covalent linkage to the N-acetylhexosamine. In some embodiments, the detection molecule may comprise a fluorescent moiety, or a radioisotope moiety.

In some embodiments, the glycoprotein, e.g., the glycosylated antibody, is produced by a clonal cell population, e.g., a clonal CHO cell population. The cell population may be in culture, e.g., or a sample from a cell culture in a bioreactor for manufacturing the glycoprotein, e.g., the glycosylated antibody. In certain embodiments, the cell population will have been transformed with at least one vector encoding a glycoprotein. The therapeutic glycoprotein may be of human, non-human or synthetic origins. In some embodiments, the glycoprotein may be for treatment of humans or veterinary indications.

In some embodiments, the method further includes a step of evaluating a biological activity of the glycoprotein produced by the cell, e.g., evaluating the presence or level of immunogenic potential of the glycoprotein, e.g., in vitro or in vivo, e.g., in an animal model.

In a second aspect, the invention comprises methods for screening one or more cells for the ability to produce an N-acetylhexosamine glycan on a glycoprotein, the method comprising:
    providing a plurality of cell populations, e.g., a plurality of CHO cell populations;
    culturing each of the plurality of cells under conditions suitable for expression of a glycoprotein;
    measuring N-acetylhexosamine glycans (e.g., N-acetylglucosamine and/or N-acetylgalactosamine) produced by each of the plurality of cells, and
    selecting one or more of the plurality of cell preparations based on the presence of a target level of N-acetylhexosamine glycans produced by the selected cell preparation.

In some embodiments, the cell population is a CHO cell population.

The N-acetylhexosamine glycans can be obtained and measured from glycoproteins produced by the cell preparations, from an isolated glycoprotein of the cell preparations, from peptides obtained from a glycoprotein produced by the cell preparations, or from glycan preparations obtained from the cell preparations or from a glycoprotein product thereof. In certain embodiments, the screening method further comprises the step of isolating a glycoprotein expression product from the cell culture and measuring for the presence or amount of an N-acetylhexosamine glycan on a glycoprotein produced by the cells in step (c). In certain embodiments, the cell screening method comprises quantifying the amount of N-acetylhexosamine glycans present on the glycoprotein preparation. In certain embodiments, step (b) of the cell screening method takes place in a bioreactor.

Each of the plurality of cell populations may comprise a different strain population, a different clonal cell population, or different samples (e.g., samples taken over time) from a cell culture used to manufacture a glycoprotein. In certain embodiments, the cell population is transformed with at least one vector encoding a glycoprotein, e.g., a glycosylated antibody, e.g., a human or humanized glycosylated antibody. In certain embodiments of the cell screening method, the glycoprotein is a secreted glycoprotein expressed from the cells.

The measuring step of the screening method may include any technique disclosed herein for identifying and/or quantifying an N-acetylhexosamine glycan on the glycoprotein.

In a third aspect, the invention includes a method for evaluating a glycoprotein preparation. The method includes measuring the amount of an N-acetylhexosamine glycan (e.g., an N-acetylglucosamine and/or N-acetylgalactosamine glycan) in a glycoprotein preparation, e.g., a glycosylated antibody preparation.

In some embodiments, the glycoprotein preparation is produced in a host cell, e.g., a prokaryotic or eukaryotic host cell. The eukaryotic cell can be, e.g., a yeast, an insect, a fungi, a plant or an animal cell (e.g., a mammalian cell). Exemplary host cells are described herein.

In some embodiment, the method includes recording the absence, presence or amount of N-aceytlhexosamine glycans in the glycoprotein preparation in a print or computer-readable medium.

In some embodiments, the method also includes comparing the measured level of N-acetylhexosamine glycan present in the glycoprotein preparation with a reference standard, such as a control or reference specification. The reference standard can be a specification (e.g., an FDA label or Physician's Insert) or quality criterion for a pharmaceutical preparation containing the glycoprotein preparation.

In some embodiment, the level of N-acetylhexosamine glycans present in a glycoprotein preparation can be measured as the level of N-acetylhexosamine glycans relative to total amount of glycans in a sample, such as a glycoprotein preparation.

In one embodiment, the technique used to measure N-acetylhexosamine glycan content includes a chromatographic method.

In one embodiment, the technique used to measure N-acetylhexosamine glycan content includes mass spectrometry (MS) methods.

In one embodiment, the technique used to measure N-acetylhexosamine glycan content includes electrophoretic methods (such as capillary electrophoresis).

In one embodiment, the technique used to measure N-acetylhexosamine glycan content includes nuclear magnetic resonance (NMR) methods.

In one embodiment, the technique used to measure N-acetylhexosamine glycan content includes monosaccharide analysis.

In one embodiment, the technique used to measure N-acetylhexosamine glycan content includes fluorescence methods.

In one embodiment, the technique used to measure N-acetylhexosamine glycan content includes UV-VIS absorbance.

In one embodiment, the technique used to measure N-acetylhexosamine glycan content includes enzymatic methods.

In one embodiment, the technique used to measure N-acetylhexosamine glycan content includes and use of a detection molecule (such as an antibody).

In another aspect, the invention includes a recombinant glycoprotein that has a different level of N-acetylhexosamine glycans than a reference glycoprotein that has the same or highly similar amino acid sequence. A highly similar amino acid sequence, as used herein, is at least 90%, 91%, 92%, 93%, 94%, 95%, 96%, 97%, 98%, or 99% identical.

In some embodiments, the reference glycoprotein is a commercially available therapeutic glycoprotein, e.g., a therapeutic glycoprotein disclosed in Table 2. The recombinant glycoprotein can have a higher or lower level of N-acetylhexosamine glycans than the reference glycoprotein, e.g., the recombinant glycoprotein can have at least 2%, 5%, 10%, 15%, 20%, 25%, 30%, 35%, 40%, 45%, 50%, 60%, 70%, 80% higher or lower level of N-acetylhexosamine glycans, e.g., as measured as a percent of total glycans, or as measured relative to the total amount of G0F, G1F, G2F and glycosylated glycopeptides. In one embodiment, the recombinant glycoprotein is an IgG1 preparation, and the recombinant glycoprotein has a level of N-acetylhexosamine glycans greater than or less than 3%, 5%, 10%, or 15% as measured relative to the total amount of G0F, G1F, G2F and glycosylated glycopeptides. In another embodiment, the recombinant glycoprotein is an IgG1 preparation, and the recombinant glycoprotein has a level of N-acetylhexosamine glycans greater than or less than 40%, 50% or 55% as measured relative to the total amount of G0F, G1F, G2F and glycosylated glycopeptides. In yet another embodiment, the recombinant glycoprotein is an IgG2 preparation, and the recombinant glycoprotein has a level of N-acetylhexosamine glycans greater than or less than 5%, 6%, 7%, 8%, 9%, 10%, 11%, 12%, 15%, 20%, or 25% as measured relative to the total amount of G0F, G1F, G2F and glycosylated glycopeptides.

In another aspect, the disclosure features a method for modulating effector function of an antibody preparation. In some embodiments, the method includes:

providing an antibody preparation; and modulating, e.g., increasing or decreasing, the N-acetylhexosamine glycan content of the antibody preparation.

In some embodiments, the method comprises increasing N-acetylhexosamine glycan content of the antibody preparation, e.g., to thereby decrease effector function of the antibody preparation. In some embodiments, the method comprises removing one or more glycan structure associated with effector function (e.g., a sialylated glycan), and e.g., the addition of an N-acetylhexosamine glycan. In other embodiments, the method comprises enzymatically or chemically modifying the glycan structure to form an N-acetylhexosamine glycan, e.g., with enzymes or chemicals described herein.

In other embodiments, the method comprises decreasing N-acetylhexosamine glycan content of the antibody preparation, e.g., to thereby increase effector function of the antibody preparation. In some embodiments, the method comprises removing one or more N-acetylhexosamine glycans, and e.g., the addition of glycan structure associated with effector function, e.g., a sialylated glycan. In other embodiments, the method comprises enzymatically or chemically modifying the glycan structure to form a glycan structure associated with increased effector function.

In another aspect, the disclosure features a method for evaluating effector function of an antibody preparation. In some embodiments, the method includes:

providing an antibody preparation; and determining the absence, presence or amount of N-acetylhexosamine glycans in the preparation.

DEFINITIONS

Figure 1:
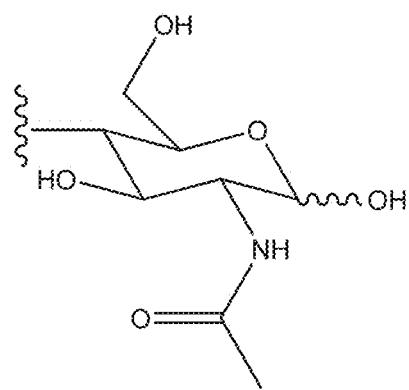
FIG. 1 is a representation of the N-acetylhexosamine glycan structures.

Unless otherwise defined herein below, all terms used herein are used in their ordinary meaning, as would be understood by one skilled in the art.

Approximately, About, Ca.: As used herein, the terms "approximately", "about" or "ca.," as applied to one or more values of interest, refer to a value that is similar to a stated reference value. In certain embodiments, the terms "approximately", "about" or "ca.," refer to a range of values that fall within 5%, 4%, 3%, 2%, 1%, or less of the stated reference value.

Detection, Detecting: As used herein, the terms "detecting," "detection" and "detecting means" are used interchangeably to refer to the determination of whether a particular chemical moiety, such as an N-acetylhexosamine (e.g., an N-acetylglucosamine and/or N-acetylgalactosamine), is present or absent in or on a compound, preparation, composition, cell or cell population. The detecting means may involve a selectable marker, or an identifiable characteristic such as a fluorescent or radioactive moiety, and may involve labeling of a reagent, compound, cell or cell population. Detection can also refer to the analysis of a compound, preparation, composition, cell or cell population, using such techniques as mass spectrometry or related methods, electrophoretic methods, nuclear magnetic resonance, chromatographic methods, or combinations of the above, to determine the presence or absence of a chemical moiety in or on a compound, preparation, composition, cell or cell population. Detection may also involve quantification of the absolute or relevant levels of the chemical moiety being detected.

Glycan: As is known in the art and used herein "glycans" are sugars. Glycans can be monomers or polymers of sugar residues, and can be linear or branched. A glycan may include natural sugar residues (e.g., glucose, N-acetylglucosamine, N-acetylgalactosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoprotein (e.g., of a glycoprotein, glycolipid, proteoglycan, etc.). The term also encompasses free glycans, including glycans that have been cleaved or otherwise released from a glycoprotein.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below). In some embodiments, a glycan preparation includes glycoproteins. In some embodiments, a glycan preparation includes released glycans.

Glycoprotein: As used herein, the term "glycoprotein" refers to a "protein" (as defined herein) that contains a peptide backbone covalently linked to one or more sugar moieties (i.e., glycans). As is understood by those skilled in the art, the peptide backbone typically comprises a linear chain of amino acid residues. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties.

Glycoprotein preparation: A "glycoprotein preparation," as that term is used herein, refers to a set of individual protein molecules, each of which comprises a particular amino acid sequence (which amino acid sequence includes at least one glycosylation site) and a plurality of the proteins have at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

Glycoprotein composition: A "glycoprotein composition" as used herein refers to a glycoprotein preparation that is in the form of a drug substance or drug product.

Glycosidase: The term "glycosidase" as used herein refers to an agent that cleaves a covalent bond between sequential sugars in a glycan or between the sugar and the backbone moiety (e.g., between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent, e.g., hydrazine.

N-glycan: The term "N-glycan," as used herein, refers to a polymer of sugars that has been released from a glycoprotein but was formerly linked to a glycoprotein via a nitrogen linkage (see definition of N-linked glycan below).

N-linked glycans: N-linked glycans are glycans that are linked to a glycoprotein via a nitrogen linkage. A diverse assortment of N-linked glycans exists, but is typically based on the common core pentasaccharide $(Man)_3(GlcNAc)(GlcNAc)$.

O-glycan: The term "O-glycan," as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation.

Modulate: The term "modulate" as used herein refers to the ability of an actor to control, within prescribed limits, the value of a parameter, such as the level of N-acetylhexosamine glycans present in a glycoprotein preparation. Thus, in some embodiments, the level of N-acetylhexosamine glycans may be modulated so that it remains within prescribed limits. In some embodiments, the level of N-acetylhexosamine glycans may be modulated so that it does not vary by more than 10.0%, 5.0%, 1.0%, 0.5% or 0.1% of a reference standard.

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Providing: The term "providing" as used herein refers to an actor obtaining a subject item, such as a cell preparation, or glycoprotein preparation, from any source including, but not limited to, obtaining by the actor's own manufacture or by the actor's receiving the item from another party. For example, a cell preparation is provided if it is made or received by any machine, person, or entity. In some embodiments, a cell preparation may be received by a machine, which may then perform one or more tests, processes, or refinements of the glycoprotein preparation. In some embodiments, a cell preparation may be received by a person. In some embodiments, a CHO cell preparation may be received from an outside entity. In some embodiments, a cell preparation may be received by a person or business performing characterization services for a second person or business.

N-acetylhexosamine glycan: The term "N-acetylhexosamine glycan" as used herein, describes the glycan structures illustrated in FIG. 1.

DETAILED DESCRIPTION OF CERTAIN EMBODIMENTS

Although host cells used for the synthesis of recombinant glycoproteins possess the intracellular machinery to produce complex glycosylation, these cells do not always possess the same complement of enzymes as the cells in which the glycoprotein is naturally expressed. Clonal selection of cell lines and variations in manufacturing conditions may also produce heterogeneity in glycoproteins expressed in cultured cells. The functional role of glycosylation in glycoprotein activity necessitates careful characterization of therapeutic products produced in cell lines.

The present disclosure is based, at least in part, on the unexpected finding that many glycoprotein preparations, e.g., glycosylated antibody preparations, contain an unusual N-linked N-acetylhexosamine glycan structure. For example, it has been found that an N-linked N-acetylhexosamine glycan can be found at the glycosylation site Asn297 of the Fc region of antibodies within a glycosylated antibody preparation. Many glycosylated antibody preparations contain this structure and, thus it is important to identify, monitor and control this aspect of glycan structure when producing glycosylated antibody preparations.

The present disclosure provides methods of analyzing the composition of glycans on glycoproteins. According to the present disclosure, glycans from glycoprotein preparations can be analyzed to determine whether they include an N-acetylhexosamine glycan. The present disclosure provides methods of detecting the absence, presence or amount of N-acetylhexosamine glycans associated with a glycoprotein preparation, e.g., a glycosylated antibody preparation, e.g., a glycosylated antibody preparation described herein, and methods of producing glycoproteins that include, include is a certain amount or lack this glycan structure.

Glycan Preparations

The present disclosure provides methods of analyzing the structure and/or composition of individual glycans within a glycan preparation, e.g., evaluating for the absence, presence or amount of N-acetylhexosamine glycans (N-acetylglucosamine and/or N-acetylgalactosamine). A glycan preparation may be obtained from a cell preparation or from a glycoprotein made by any method available in the art. In general, obtaining a glycan preparation comprises steps of (1) obtaining a cell or glycoprotein preparation; and (2) optionally releasing glycans from the cell or glycoprotein preparation. In some embodiments, obtaining a glycan preparation optionally comprises labeling the glycan preparation with a detectable label.

Glycoprotein Preparations

Methods for recombinant production of glycoproteins have been described. Glycoproteins secreted by cultured cells can be isolated and purified by any available means, such as anion-exchange chromatography, reversed-phase chromatography, gel filtration, immunoaffinity chromatography, and combinations thereof.

N-Linked Glycan Preparation

In some embodiments, an N-glycan preparation is obtained by providing a glycoprotein population and removing N-linked glycans from the glycoproteins in the population.

In some embodiments, N-linked glycans are removed from glycoproteins (e.g., glycoproteins) by digestion. Generally, glycanases to be used in accordance with the present disclosure cleave between GlcNAc-Asn, GlcNAc-GlcNAc, or Man-GlcNAc residues of the core. Exemplary enzymes which can be used to remove N-linked glycans from glycoproteins include, but are not limited to, N-glycanase F and/or N-glycanase-A, O-glycanase and/or Endo H.

In some embodiments, N-linked glycans are removed from glycoproteins by chemical cleavage. To give but a few examples, hydrazine, sodium borohydride, and/or trifluoromethanesulfonic acid (TFMS) can be used to remove glycans from a glycoprotein.

O-Linked Glycan Preparation

In some embodiments, an O-linked glycan preparation is obtained by providing a glycoprotein (e.g., glycoprotein) population and removing O-linked glycans from glycoproteins in the population.

In some embodiments, O-linked glycans are removed from glycoproteins (e.g., glycoproteins) by beta elimination. In some embodiments, O-linked glycans are removed from glycoproteins (e.g., glycoproteins) by reductive beta elimination. In some embodiments, O-glycans are removed from glycoproteins (e.g., glycoproteins) by non-reductive beta elimination.

In some embodiments, O-linked glycans are removed from a glycoprotein (e.g., a glycoprotein) preparation by incubating the preparation in a solution that includes alkaline tetrahydroborate. In some embodiments, tetradeuterioborate is used, e.g., to incorporate a deuterium label to facilitate detection of O-linked glycans. In various exemplary methods, a glycoprotein preparation is incubated in a solution containing 0.8-1.0 M $NaBH_4$ and 0.05-0.1 M NaOH at 42-45° C. for 2-24 hours. A reaction to remove O-linked glycans can be terminated by the addition of acid (e.g., 1.0 M HCl).

In some embodiments, O-linked glycans are removed from a glycoprotein preparation by incubating the preparation in a solution that includes NaOH. In various exemplary methods, a glycoprotein is incubated in a solution containing 50-200 mM NaOH at 27-45° C. for 2-48 hours. A reaction can be terminated by the addition of acid.

In some embodiments, O-linked glycans are removed from a glycoprotein preparation by incubating the preparation in a solution that includes $NH_4OH$. In various exemplary methods, a glycoprotein is incubated in a solution containing 25-28% $NH_4OH$ at 45-60° C. for 2-40 hours. The reaction can be terminated by removing the $NH_4OH$ under vacuum. In some embodiments, the solution includes ammonium carbonate (e.g., at a saturating concentration). In some embodiments, the $NH_4OH$-treated preparation is treated with acid (e.g., boric acid).

In some embodiments, O-linked glycans are removed from a glycoprotein preparation by incubating the preparation in an aqueous solution that includes ethylamine (e.g., ethylamine at about 70%) or methylamine (e.g., methylamine at about 40%), for about 4-24 hours.

In some embodiments, an O-linked glycan preparation is obtained from a glycoprotein population from which N-linked glycans have been removed.

Labeling Glycans

In some embodiments, labels can be associated with glycans before or after release from a glycoprotein. N-linked glycans or O-linked glycans (e.g., N-glycans that have been removed from a glycoprotein population) can be associated with one or more detectable labels. Detectable labels are typically associated with the reducing ends of glycans. In some embodiments, detectable labels are fluorescent moieties. Exemplary fluorophores that can be used in accordance with the present disclosure include, but are not limited to, 2-aminobenzoic acid (2AA), 2-aminobenzamide (2AB), and/or 2-aminopurine (2AP). In general, fluorophores for use in accordance with the present disclosure are characterized by having reactivity with the reducing end of an oligosaccharide and/or monosaccharide under conditions that do not damage and/or destroy the glycan. In some embodiments, fluorescent moieties are attached to reducing ends directly. For example, direct attachment can be accomplished by direct conjugation by reductive amination. In some embodiments, fluorescent moieties are attached to reducing ends indirectly. For example, indirect attachment can be accomplished by a reactive linker arm.

In some embodiments, detectable labels comprise radioactive moieties or isotopically-labelled molecules. Exemplary radioactive moieties that can be used in accordance with the present disclosure include, but are not limited to, tritium ($^3H$), deuterium ($^2H$), and/or $^{35}S$. Typically, such moieties are directly attached to or otherwise associated with the fluorophore. To give but one example of a radioactive fluorophore, 2AP can be modified such that all hydrogens are deuterated.

Release of Glycans

The present disclosure provides improved methods of determining glycosylation patterns of glycoproteins. Such methods can involve subjecting a glycan population to one or more exoglycosidases and analyzing the structure and/or composition of the digestion products. In some embodiments, exoglycosidases used in accordance with the present disclosure recognize and cleave only one particular type of glycosidic linkage. In some embodiments, exoglycosidases used in accordance with the present disclosure recognize and cleave more than one particular type of glycosidic linkage. Among the exoglycosidases which may be useful for the present invention are α-galactosidases, β-galactosidases; hexosaminidases, mannosidases; and combinations thereof.

Exoglycosidases

Exoglycosidases are enzymes which cleave terminal glycosidic bonds from the non-reducing end of glycans. They are typically highly specific to particular monosaccharide linkages and anomericity (α/β). In some embodiments, neighboring branching patterns can affect exoglycosidase specificity. Exoglycosidase treatment usually results in glycans of standard antennary linkages being cleaved down to the pentasaccharide core (M3N2) containing 3 mannose and 2 GlcNAc residues. However, unusually-modified species (e.g., antennary or core fucosylated species, high-mannose and hybrid glycans, lactosamine-extended glycans, sulfated glycans, phosphorylated glycans, etc.) are resistant to exoglycosidase treatment and can be chromatographically resolved and quantified relative to the M3N2 pentasaccharide.

Exemplary exoglycosidases that can be used in accordance with the present disclosure include, but are not limited to, sialidase, galactosidase, hexosaminidase, fucosidase, and mannosidase. Exoglycosidases can be obtained from any source, including commercial sources or by isolation and/or purification from a cellular source (e.g., bacteria, yeast, plant, etc.).

In some embodiments, exoglycosidases (e.g., sialidases, galactosidases, hexosaminidases, fucosidases, and mannosidases) can be divided into multiple categories or "subsets." In some embodiments, the different subsets display different abilities to cleave different types of linkages. Table 1 presents some exemplary exoglycosidases, their linkage specificities, and the organism from which each is derived. One of ordinary skill in the art will appreciate that this is an exemplary, not a comprehensive, list of exoglycosidases, and that any exoglycosidase having any linkage specificity may be used in accordance with the present disclosure.

TABLE 1

Exoglycosidases

| Enzyme class | EC #* | Activity | Organism |
|---|---|---|---|
| α-Sialidase | 3.2.1.18 | α-2/3,6,8 (usually not linkage-specific) | Arthrobacter ureafaciens Vibrio cholerae Clostridium perfringens |
| | | α-2,3 (NeuAc from oligosaccharides) | Salmonella typhimurium Streptococcus pneumonia |
| | | α-2/3,6 (NeuAc from complex) | Clostridium perfringens |
| β-Galactosidase | 3.2.1.23 | β-1/3,4,6 Gal linkages | Bovine testis Xanthamonas species Streptococcus species E. coli |
| | | β-1/4,6 Gal linkages | Jack bean |
| | | β-1,4 Gal linkage | Streptococcus pneumonia |
| | | β-1,3-Gal linkage | E. coli Xanthomonas species |
| | | β-1/3,6-Gal linkages | Xanthomonas species E. coli |
| β-Hexosaminidase | 3.2.1.52 3.2.1.30 | β-1/2,3,4,6 hexosamines | Streptococcus plicatus Streptococcus pneumonia Bacteroides Jack bean |
| α-Fucosidase | 3.2.1.51 3.2.1.111 | α-1-3,4-Fuc (usually de-glycosylate Lewis structure) | Xanthomonas Almond meal |
| | | α-1/2,3,4,6-Fuc (usually has broad specificity) | Bovine kidney C. meningosepticum |
| | | α-1,6-Fuc | E. coli |
| | | α-1,2-Fuc | Xanthomonas |
| α-Mannosidase | 3.2.1.24 | α-1/2,3,6-Man | Jack bean |
| | | α-1/2,3-Man | Xanthomonas manihotis |
| | | α-1,6-Man (typically a core mannosidase) | Xanthomonas species |
| | | α-1,2-Man | Aspergillus saitoi |
| β-Mannosidase | 3.2.1.25 | α-1,4-Man | Helix pomatia |

"EC #" refers to Enzyme Commission registration number

According to the present disclosure, a glycan population can be digested with any exoglycosidase or any set of exoglycosidases. In general, exoglycosidase reactions take place under conditions that are compatible with enzyme activity. For example, pH, temperature, reaction solution components and concentration (e.g., salt, detergent, etc.), and length of reaction time can be optimized in order to achieve a desired level of exoglycosidase activity. See, e.g., WO 2008/130926, the contents of which are herein incorporated by reference.

Analysis of Glycan Structure and Activity

In general, methods in accordance with the disclosure comprise subjecting a glycan preparation to analysis to determine whether glycoproteins in the preparation include an N-acetylhexosamine glycan structure. In some embodiments, the analysis comprises comparing the structure and/or function of glycans in one glycoprotein preparation from one source to structure and/or function of glycans in at least one other glycoprotein preparation from another source. In some embodiments, the analysis comprises comparing the structure and/or function of glycans in one or more of the samples to structure and/or function of glycans in a reference sample.

Structure and composition of glycans can be analyzed by any available method. In some embodiments, glycan structure and composition are analyzed by chromatographic methods, mass spectrometry (MS) methods, chromatographic methods followed by MS, electrophoretic methods, electrophoretic methods followed by MS, nuclear magnetic resonance (NMR) methods, and combinations thereof.

In some embodiments, glycan structure and composition can be analyzed by chromatographic methods, including but not limited to, liquid chromatography (LC), high performance liquid chromatography (HPLC), ultra performance liquid chromatography (UPLC), thin layer chromatography (TLC), amide column chromatography, and combinations thereof.

In some embodiments, glycan structure and composition can be analyzed by mass spectrometry (MS) and related methods, including but not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, glycan structure and composition can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, glycan structure and composition can be analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some embodiments, techniques described herein may be combined with one or more other technologies for the detection, analysis, and/or isolation of glycans or glycoproteins. For example, in certain embodiments, glycans are analyzed in accordance with the present disclosure using one or more available methods (to give but a few examples, see Anumula, Anal. Biochem. 350(1):1, 2006; Hara et al., Anal. Biochem., 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some embodiments, glycans are characterized using one or more of chromatographic methods, electrophoretic methods, nuclear magnetic resonance methods, and combinations thereof. Exemplary such methods include, for example, NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof. Those of ordinary skill in the art will be aware of other techniques that can be used to characterize glycans together with the methods described herein.

In some embodiments, methods described herein allow for detection of glycan species (such as an N-acetylhexosamine glycan (e.g., an N-acetylglucosamine and/or N-acetylgalactosamine glycan) that are present at low levels within a population of glycans. For example, the present methods allow for detection of glycan species that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of particular structures (e.g., an N-acetylhexosamine glycan (e.g., an N-acetylglucosamine and/or N-acetylgalactosamine glycan)) that are present at low levels within a population of glycans. For example, the present methods allow for detection of particular structures that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of relative levels of individual glycan species within a population of glycans. For example, the area under each peak of a liquid chromatograph can be measured and expressed as a percentage of the total. Such an analysis provides a relative percent amount of each glycan species within a population of glycans. In another example, relative levels of individual glycan species are determined from areas of peaks in a 1D-NMR experiment, or from volumes of cross peaks from a 1H-15HSQC spectrum (e.g., with correction based on responses from standards), or by relative quantitation by comparing the same peak across samples.

In some embodiments, a biological activity of a glycoprotein preparation (e.g., a glycosylated antibody preparation) is assessed. Biological activity of the glycoprotein preparation can be analyzed by any available method. In some embodiments, a binding activity of a glycoprotein is assessed (e.g., binding to a receptor). In some embodiments, a therapeutic activity of a glycoprotein is assessed (e.g., an activity of a glycoprotein in decreasing severity or symptom of a disease or condition, or in delaying appearance of a symptom of a disease or condition). In some embodiments, a pharmacologic activity of a glycoprotein is assessed (e.g., bioavailability, pharmacokinetics, pharmacodynamics). For methods of analyzing bioavailability, pharmacokinetics, and pharmacodynamics of glycoprotein therapeutics, see, e.g., Weiner et al., J Pharm Biomed Anal. 15(5):571-9, 1997; Srinivas et al., J. Pharm. Sci. 85(1):1-4, 1996; and Srinivas et al., Pharm. Res. 14(7):911-6, 1997.

As would be understood to one of skill in the art, the particular biological activity or therapeutic activity that can be tested will vary depending on the particular glycoprotein.

The potential adverse activity or toxicity (e.g., propensity to cause hypertension, allergic reactions, thrombotic events, seizures, or other adverse events) of glycoprotein preparations can be analyzed by any available method. In some embodiments, immunogenicity of a glycoprotein preparation is assessed, e.g., by determining whether the preparation elicits an antibody response in a subject.

In various embodiments, biological activity, therapeutic activity, etc., of a glycoprotein preparation that includes an N-acetylhexosamine glycan is compared to a glycoprotein preparation that does not include or includes at background levels an N-acetylhexosamine glycan. In various embodiments, biological activity, therapeutic activity, etc., of a glycoprotein preparation having N-acetylhexosamine glycans is compared to a glycoprotein preparation having a different level of N-acetylhexosamine glycans.

Applications

Methods of the present disclosure can be utilized to analyze glycans from glycoproteins in any of a variety of states including, for instance, free glycans, glycoproteins (e.g., glycopeptides, glycolipids, proteoglycans, etc.), cell-associated glycans (e.g., nucleus-, cytoplasm-, cell-membrane-associated glycans, etc.); glycans associated with cellular, extracellular, intracellular, and/or subcellular components (e.g., proteins); glycans in extracellular space (e.g., cell culture medium), etc.

Methods of the present disclosure may be used in one or more stages of process development for the production of a therapeutic or other commercially relevant glycoprotein. For example, the methods described herein can be used to evaluate a production parameter or parameters using to produce a glycoprotein preparation, to compare glycoprotein preparations produced by different production parameters, and to determine and/or select a production parameter or parameters for a glycoprotein preparation such that a particular glycan structure can be obtained upon production of a glycoprotein preparation. A production parameter as used herein is a parameter or element in a production process. Production parameters that can be selected include, e.g., the cell or cell line used to produce the glycoprotein preparation, the culture medium, culture process or bioreactor variables (e.g., batch, fed-batch, or perfusion), purification process and formulation of a glycoprotein preparation. Exemplary production parameters include: 1) the types of host; 2) genetics of the host; 3) media type; 4) fermentation platform; 5) purification steps; and 6) formulation.

The present disclosure can also be utilized to monitor the extent and/or type of glycosylation occurring in a particular cell culture (e.g., the extent of N-acetylhexosamine glycans in glycoprotein preparation produced in the cell culture), thereby allowing adjustment or possibly termination of the culture in order, for example, to achieve a particular desired glycosylation pattern or to avoid development of a particular undesired glycosylation pattern.

The present disclosure can also be utilized to assess glycosylation characteristics of cells or cell lines (e.g., CHO cell lines) that are being considered for production of a particular desired glycoprotein (for example, even before the cells or cell lines have been engineered to produce the glycoprotein, or to produce the glycoprotein at a commercially relevant level).

For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible (e.g., having a degree of N-acetylhexosamine glycan content which is close to that of the pharmaceutical product), e.g., whether or not it is being produced by exactly the same route. As used herein, "close" refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

For example, in some embodiments, methods for monitoring production of a glycoprotein may comprise steps of (i) during production of a glycoprotein, removing at least first and second glycan-containing samples from the production system; (ii) subjecting each of the first and second glycan-containing samples to an analysis to determine whether a particular modification is present (e.g., an N-acetylhexosamine glycan); and (iii) comparing the products obtained from the first glycan-containing sample with those obtained from the second glycan-containing sample so that differences are determined and therefore progress of glycoprotein production is monitored. In some embodiments, the production system comprises CHO cells.

Whether or not monitoring production of a particular target protein for quality control purposes, the present disclosure may be utilized, for example, to monitor glycosylation at particular stages of development, or under particular growth conditions.

In some embodiments, methods described herein can be used to characterize, modulate and/or control or compare the quality of therapeutic products. To give but one example, the present methodologies can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the present disclosure can facilitate real time analysis of glycosylation in production systems for therapeutic proteins, and hence, modulation of the glycosylation may be achieved.

In some embodiments, the glycoprotein preparation is a glycosylated antibody preparation. The term "antibody" refers to a protein that includes at least one immunoglobulin variable domain (variable region) or immunoglobulin variable domain (variable region) sequence. For example, an antibody can include a heavy (H) chain variable region (abbreviated herein as VH or HV), and a light (L) chain variable region (abbreviated herein as VL or LV). In another example, an antibody includes two heavy (H) chain variable regions and two light (L) chain variable regions. The term "antibody" encompasses antigen-binding fragments of antibodies as well as complete antibodies. The term "antigen-binding fragment" of a full length antibody refers to one or more fragments of a full-length antibody that retain the ability to specifically bind to a target of interest.

An antibody can have the structural features of IgA, IgG, IgE, IgD, IgM (as well as subtypes thereof). Antibodies may be from any source, but primate (human and non-human primate) and primatized are preferred.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

In one embodiment, the glycosylated antibody has one or more regions that are human or effectively human. For example, one or more of the variable regions can be human or effectively human. For example, one or more of the CDRs can be human, e.g., HC CDR1, HC CDR2, HC CDR3, LC CDR1, LC CDR2, and/or LC CDR3. Each of the light chain (LC) and/or heavy chain (HC) CDRs can be human. HC CDR3 can be human. One or more of the framework regions can be human, e.g., FR1, FR2, FR3, and/or FR4 of the HC and/or LC. For example, the Fc region can be human. In one embodiment, all the framework regions are human.

Representative glycoprotein products include, for example, the glycosylated antibodies provided in Table 2:

TABLE 2

Exemplary Commercially Available Glycoprotein Products

| Protein Product | Reference Listed Drug |
| --- | --- |
| Alefacept; recombinant, dimeric fusion protein LFA3-Ig | Amevive ® |
| Bevacizumab | Avastin ™ |
| Tositumomab | BEXXAR ® |
| Alemtuzumab | Campath ® |
| acritumomab; technetium-99 labeled | CEA-Scan ® |
| crotalidae polyvalent immune Fab, ovine | CroFab ™ |
| digoxin immune Fab [ovine] | DigiFab ™ |
| Etanercept | ENBREL ® |
| Cetuximab | Erbitux ™ |
| Trastuzumab | Herceptin ® |
| Somatotropin | Humatrope ® |
| Adalimumab | HUMIRA ™ |
| Ranibizumab | LUCENTIS ® |
| gemtuzumab ozogamicin | Mylotarg ™ |
| Fanolesomab | NeutroSpec ™ (formerly LeuTech ®) |
| immunoglobulin intravenous | Octagam ® |
| abatacept, fully human soluble fusion protein | Orencia ™ |
| muromomab-CD3 | Orthoclone OKT3 ® |
| Infliximab | REMICADE ® |
| Abciximab | ReoPro ™ |
| Rituximab | Rituxan ™ |
| Basiliximab | Simulect ® |
| Eculizumab | SOLIRIS (R) |
| Palivizumab; recombinantly produced, humanized mAb | Synagis ™ |
| Natalizumab | TYSABRI ® |
| human immune globulin intravenous 5% and 10% solutions | Venoglobulin-S ® |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |

In some embodiments, the disclosure provides methods in which glycans from glycoproteins from different sources or samples are compared with one another. In some such examples, multiple samples from the same source (e.g., from the same CHO cell source) are obtained over time, so that changes in glycosylation patterns (and particularly in cell surface glycosylation patterns) (e.g., changes in the presence or extent of N-acetylhexosamine glycans) are monitored. In some embodiments, one of the samples is a historical sample or a record of a historical sample. In some embodiments, one of the samples is a reference sample.

In some embodiments, the disclosure provides methods in which glycans from glycoproteins expressed by different cell sources are compared with one another. In some embodiments, one or more of the compared cell sources are CHO cells.

In some embodiments, glycans from different cell culture samples prepared under different production parameters (e.g., cell type, culture type (e.g., continuous feed vs. batch feed, etc.), culture conditions (e.g., type of media, presence or concentration of particular component of particular medium (a), osmolarity, pH, temperature, timing or degree of shift in one or more components such as osmolarity, pH, temperature, etc.), culture time, isolation steps, etc.) but are otherwise identical, are compared, so that effects of the selected production parameter on glycosylation are determined. In certain embodiments, glycans from different cell culture samples prepared under conditions that differ in a single selected production parameter are compared so that effects of the single selected production parameter on glycosylation patterns (e.g., the absence, presence, or extent of N-acetylhexosamine glycans) are determined. Among other applications, therefore, use of techniques as described herein may facilitate determination of the effects of particular production parameters on glycosylation patterns in cells.

In some embodiments, glycans from different batches of a glycoprotein, whether prepared by the same method or by different methods, and whether prepared simultaneously or separately, are compared. In such embodiments, the present disclosure facilitates quality control of a glycoprotein preparation. Alternatively or additionally, some such embodiments facilitate monitoring of progress of a particular culture producing a glycoprotein (e.g., when samples are removed from the culture at different time points and are analyzed and compared to one another). In some examples, multiple samples from the same source are obtained over time, so that changes in glycosylation patterns are monitored. In some embodiments, glycan-containing samples are removed at about 30 second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

In some embodiments, methods in accordance with the disclosure may be used to monitor the glycosylation pattern of glycoproteins during the course of their production by cells. For example, production of a glycoprotein (e.g., commercial production) may involve steps of (1) culturing cells that produce the glycoprotein, (2) obtaining samples at regular or irregular intervals during the culturing, and (3) analyzing the glycosylation pattern of produced glycoprotein(s) in obtained sample(s). In some embodiments, such methods may comprise a step of comparing the glycosylation patterns of produced glycoprotein(s) in obtained samples to one another. In some embodiments, such methods may comprise a step of comparing glycosylation patterns of produced glycoprotein(s) in obtained sample(s) to the glycosylation pattern of a reference sample.

In some embodiments, methods in accordance with the disclosure may be used to monitor the glycosylation pattern of glycoproteins over the course of storage. For example, the method can include obtaining samples at regular or irregular intervals during the storage of a glycoprotein preparation, and (3) analyzing the glycosylation pattern of glycoprotein(s) in obtained sample(s). In some embodiments, such methods may comprise a step of comparing the glycosylation patterns of the glycoprotein(s) in obtained samples to one another. In some embodiments, such methods may comprise a step of comparing glycosylation patterns of the glycoprotein(s) in obtained sample(s) to the glycosylation pattern of a reference sample.

In any of these embodiments, features of the glycan analysis can be recorded, for example in a quality control record. As indicated above, in some embodiments, a comparison is with a historical record of a prior or standard batch and/or with a reference sample of glycoprotein.

In some embodiments, glycans from different batches of a particular glycoprotein, whether prepared by the same method or by different methods, and whether prepared simultaneously or separately, are compared to one another and/or to a reference sample. In some embodiments, batch-to-batch comparison may comprise the steps of (i) providing a first glycan preparation from a first batch of the glycoprotein; (ii) providing a second glycan preparation from a second batch of the glycoprotein; (iii) subjecting each of the first and second glycan preparations to analysis procedure; and (iv) comparing the results of the analysis obtained from the first glycan preparation with the cleavage products obtained from the second preparation so that consistency of the two batches is assessed. In some embodiments, glycan preparations can be provided by removing at least one glycan from at least one glycoprotein from a batch and, optionally, isolating removed glycans. In some embodiments, glycan preparations may be labeled as described herein (e.g., fluorescently and/or radioactively; e.g., prior to and/or after isolation).

In some embodiments, the present disclosure facilitates quality control of a glycoprotein preparation. Features of the glycan analysis can be recorded, for example in a quality control record. As indicated above, in some embodiments, a comparison is with a historical record of a prior or standard batch of glycoprotein. In some embodiments, a comparison is with a reference glycoprotein sample.

In certain embodiments, the present disclosure may be utilized in studies to modify the glycosylation characteristics of a cell, for example to establish a cell line and/or culture conditions with one or more desirable glycosylation characteristics, e.g., a cell line that produces glycoproteins having, having a certain amount or lacking an N-acetylhexosamine glycan. Such a cell line and/or culture conditions can then be utilized, if desired, for production of a particular target glycoprotein for which such glycosylation characteristic(s) is/are expected to be beneficial. In particular embodiments, the cell is a CHO cell.

According to the present disclosure, techniques described herein can be used to detect desirable or undesirable glycans, for example to detect or quantify the presence of one or more contaminants in a glycoprotein product, or to detect or quantify the presence of one or more active or desired species.

In certain embodiments, methods described herein facilitate detection of glycans that are present at very low levels in a source (e.g., a biological sample, glycan preparation, etc.). In such embodiments, it is possible to detect and/or optionally quantify the levels of glycans that are present at levels less than about 10%, 5%, 4%, 3%, 2%, 1.5%, 1%, 0.75%, 0.5%, 0.25%, 0.1%, 0.075%, 0.05%, 0.025%, or 0.01% within a population of glycans. In some embodiments, it is possible to detect and/or optionally quantify the levels of glycans comprising between 0.1% and 5%, e.g., between 0.1% and 2%, e.g., between 0.1% and 1% of a glycan preparation.

In some embodiments, methods described herein allow for detection of relative levels of individual glycan species within a population of glycans. For example, the area under each peak of a liquid chromatograph can be measured and expressed as a percentage of the total. Such an analysis provides a relative percent amount of each glycan species within a population of glycans. In some embodiments, methods described herein allow for the manufacture of a glycoprotein, e.g., a glycoprotein containing an N-acetylhexosamine glycan, e.g., N-acetylglucosamine or N-acetylgalactosamine. For example, the manufacture of a glycoprotein (e.g., commercial production) may involve steps of (1) culturing cells that produce the glycoprotein, (2) obtaining samples of the glycoprotein (e.g., at regular or irregular intervals during the culturing, and/or at the end of a culturing process) and (3) analyzing the glycosylation pattern of produced glycoprotein(s) in obtained sample(s) for the presence, absence and/or amount of an N-acetylhexosamine glycan, e.g., N-acetylglucosamine or N-acetylgalactosamine. In some embodiments, such methods may comprise a step of comparing the glycosylation patterns of produced glycoprotein(s) in obtained samples to a reference, e.g., comparing the presence, absence and/or amount of an N-acetylhexosamine glycan, e.g., N-acetylglucosamine or N-acetylgalactosamine in the produced glycoprotein, to a reference, such as a pharmaceutical specification, e.g., a pharmaceutical specification for the produced glycoprotein for the presence, absence and/or amount of an N-acetylhexosamine glycan, e.g., N-acetylglucosamine or N-acetylgalactosamine. In some embodiments, the methods may comprise a step of comparing glycosylation patterns of produced glycoprotein(s) in obtained sample(s) to the glycosylation pattern of a reference sample.

In some embodiments, the method comprises further processing of the glycoprotein, e.g., the further processing can include combining the glycoprotein preparation with a second component, e.g., an excipient or buffer. In one embodiment, the further processing can include one or more of: formulating the glycoprotein preparation; processing the glycoprotein n preparation into a drug product; combining the glycoprotein preparation with a second component, e.g., an excipient or buffer; changing the concentration of the glycoprotein in the preparation; lyophilizing the glycoprotein preparation; combining a first and second aliquot of the glycoprotein to provide a third, larger, aliquot; dividing the glycoprotein preparation into smaller aliquots; disposing the glycoprotein preparation into a container, e.g., a gas or liquid tight container; packaging the glycoprotein preparation; associating a container comprising the glycoprotein preparation with a label; shipping or moving the glycoprotein preparation to a different location.

The present disclosure will be more specifically illustrated with reference to the following examples. However, it should be understood that the present disclosure is not limited by these examples in any manner.

One of skill in the art may readily envision various other combinations within the scope of the present invention, considering the example with reference to the specification herein provided.

EXAMPLES

Example 1

Figure 2:
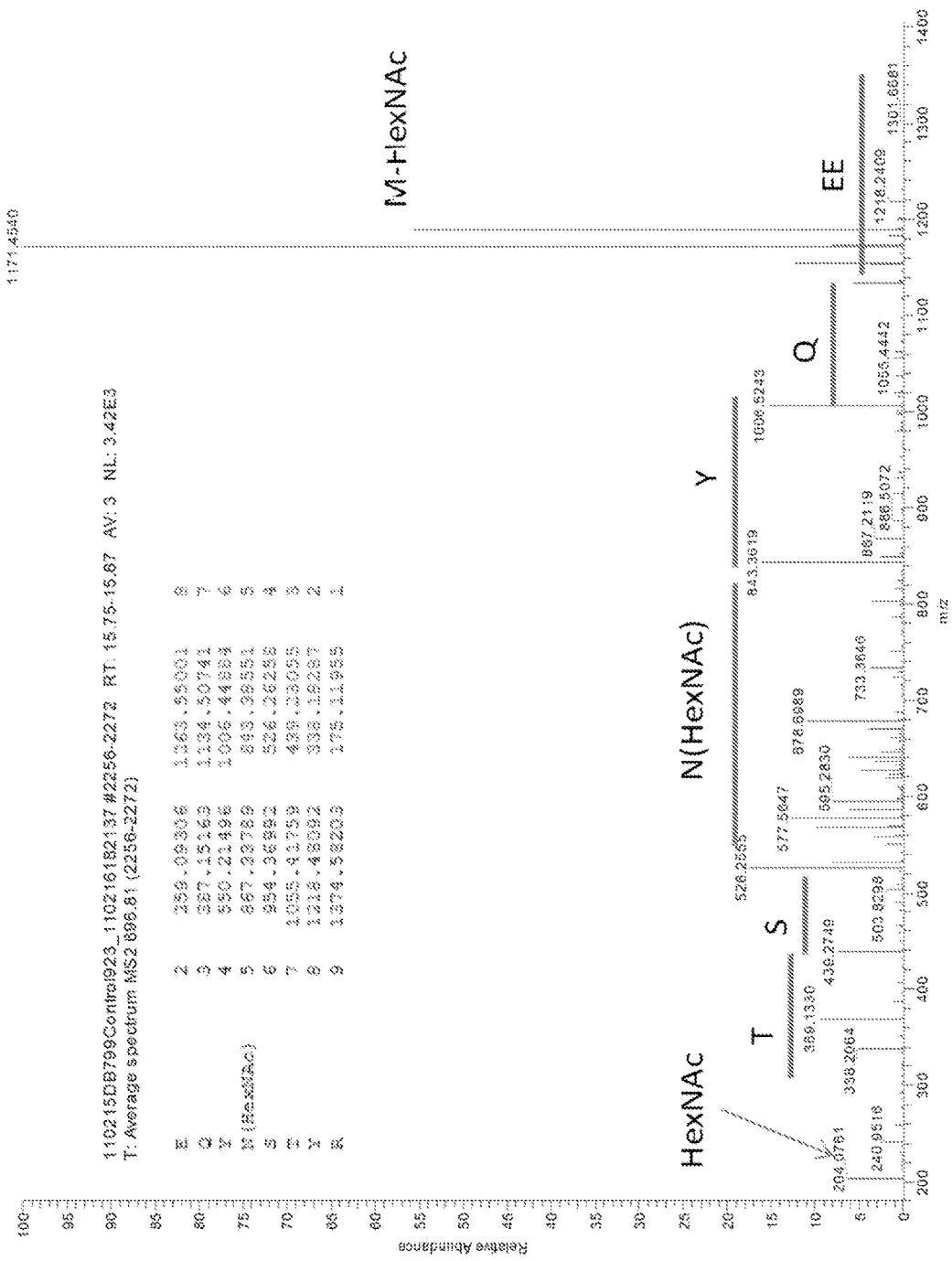
FIG. 2 depicts MS/MS fragmentation of IgG Fc glycopeptides containing a single N-linked N-acetylhexosamine glycan. The fragmentation pattern places the modification in the Asn residue, residue 297, in the middle of the sequence (SEQ ID NO: 1).

The truncated N-linked glycan identified was unexpected based on the biosynthetic glycosylation pathway as it is understood. In general, a glycoprotein proceeds through the standard glycosylation cascade resulting in a number of potential N-linked glycan species, all of which contain at least a core structure containing 2 GlcNAc moieties and 3 mannose residues. This species identified consists of only a single N-acetylhexosamine linked to Asn297 in the Fc domain of the antibody. The species was identified though mass spectrometric analysis of the tryptic digest of a monoclonal antibody. A species having a mass 203 Da higher than the expected mass of the non-glycosylated peptide was observed as the [M+2H].sup.2+ ion with an m/z of 696.8 (which is the mass of the peptide with one HexNAc). MS/MS interrogation of this species revealed the peptide contains a hexosamine residue linked to the single asparagine residue that comprises SEQ ID NO: 1 (FIG. 2).

Figure 3:
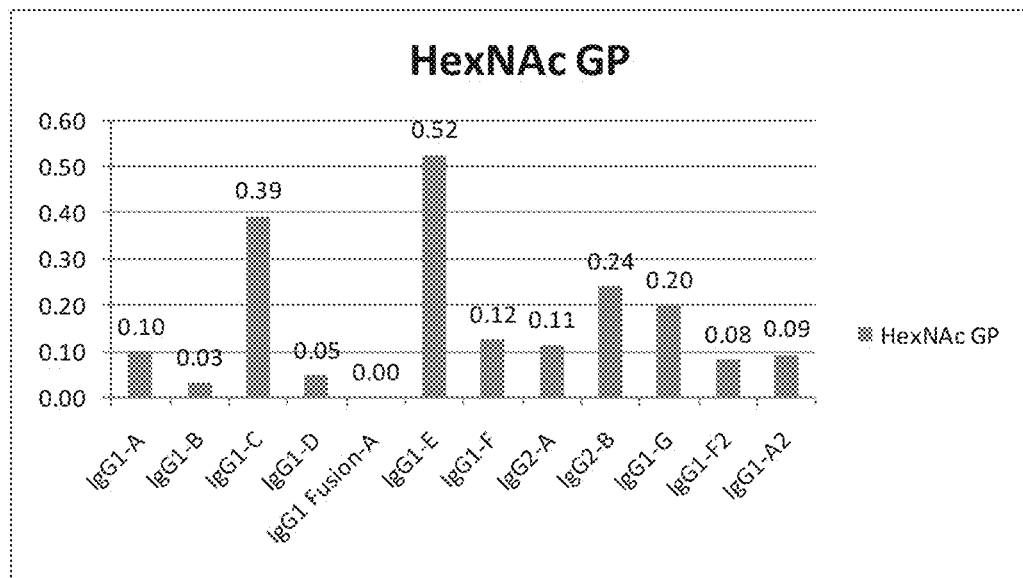
FIG. 3 is a graph depicting the percentage of truncated N-linked N-acetylhexosamine glycan present in commercially available IgG glycoproteins. Relative abundance of the N-acetylhexosamine glycan containing glycoproteins is calculated based upon the abundance of the G0F, G1F, G2F and the aglycosyl glycopeptides. These species comprise more than 85% of the glycan composition for each of the commercially available IgGs tested.

This species was also found in several commercial antibodies at varying levels (FIG. 3). Peptides were derived from each of the commercially available antibody products through the use of enzymatic cleavage (i.e. trypsin). Peptides were reduced and alkylated and analyzed by LC-MS with MS/MS used for peptide sequencing. The amino acid sequence from peptide sequencing was used to determine the identity of the peptide. Glycopeptides were observed as a mass shift relative to the non-glycosylated peptide. The relative abundance of HexNAc-glycopeptide in various commercially available antibody products was calculated based on the abundance of the G0F (fucosylated, but no galactose residues biantennary glycan), G1F (fucosylated and one galactose residue biantennary glycan), G2F (fucosylated and two galactose residues, biantennary glycan), and the aglycosyl glycopeptides.

The presence of this species was not confined to a particular class of antibody as it was identified in both IgG1 and IgG2 therapeutics.

Procedure Used to Analyze the Glycan Species:

Peptides were derived from the drug substance through the use of enzymatic cleavage (i.e. trypsin). Peptides were reduced and alkylated and analyzed by LC-MS with MS/MS used for peptide sequencing. The amino acid sequence from peptide sequencing was used to determine the identity of the peptide. Glycopeptides were observed as a mass shift relative to the non-glycosylated peptide.

This data illustrates the presence of an N-linked N-acetylhexosamine in the glycosylated monoclonal antibody. FIG. 2 shows the fluorescence chromatogram of a fraction of glycans derived from the monoclonal antibody.

Extensions and Alternatives

While the methods has been particularly shown and described with reference to specific illustrative embodiments, it should be understood that various changes in form and detail may be made without departing from the spirit and scope of the present disclosure. Therefore, all embodiments that come within the scope and spirit of the methods, and equivalents thereto, are intended to be claimed. The claims, descriptions and diagrams of the methods, systems, and assays of the present disclosure should not be read as limited to the described order of elements unless stated to that effect.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way. While the methods have been described in conjunction with various embodiments and examples, it is not intended that the methods be limited to such embodiments or examples. On the contrary, the methods encompass various alternatives, modifications, and equivalents, as will be appreciated by those of skill in the art.

The invention claimed is:

1. A method for manufacturing an antibody preparation, the method comprising:

culturing mammalian cells to produce a recombinant antibody preparation;

determining a level of an N-linked glycan consisting of a single N-acetylglucosamine residue in the produced preparation; and processing the antibody preparation as a pharmaceutical product based upon the determination.

2. The method of claim 1, further comprising comparing the determined level of N-linked glycans consisting of a single N-acetylglucosamine residue to a reference value for the antibody preparation for the level of N-linked glycans consisting of a single N-acetylglucosamine residue.

3. The method of claim 1, wherein the determining step comprises the use of a method for identifying or quantifying N-linked glycans consisting of a single N-acetylglucosamine residue selected from the group consisting of: chromatographic methods, mass spectrometry (MS) methods, electrophoretic methods, nuclear magnetic resonance (NMR) methods, monosaccharide analysis, fluorescence methods, UV-VIS absorbance, enzymatic methods, use of a detection molecule, and combinations thereof.

4. The method of claim 1, wherein the cells are cultured in a bioreactor.

5. The method of claim 1, wherein the processing step comprises disposing the antibody preparation into a container and the container is a gas or liquid tight container.

6. The method of claim 1, wherein the cells are CHO cells.

7. The method of claim 1, wherein the processing step comprises one or more of: formulating the antibody preparation; processing the antibody preparation into a drug product; combining the antibody preparation with a second component; lyophilizing the antibody preparation.

8. The method of claim 1, wherein the processing step comprises formulating the antibody preparation.

9. The method of claim 1, wherein the processing step comprises processing the antibody preparation into a drug product.

10. The method of claim 1, wherein the processing step comprises lyophilizing the antibody preparation.

11. The method of claim 1, wherein the processing step comprises one or more of: formulating the antibody preparation; processing the antibody preparation into a drug product; combining the antibody preparation with a second component; changing the concentration of the antibody in the preparation; lyophilizing the antibody preparation; combining a first and second aliquot of the antibody to provide a third, larger, aliquot; dividing the antibody preparation into smaller aliquots; disposing the antibody preparation into a container; packaging the antibody preparation; associating a container comprising the antibody preparation with a label; shipping or moving the antibody preparation to a different location.

12. The method of claim 1, wherein the antibody is a therapeutic antibody.

13. The method of claim 1, wherein the antibody preparation comprises an N-linked glycan consisting of a single N-acetylglucosamine residue.

14. The method of claim 1, wherein the antibody preparation comprises an N-linked glycan consisting of a single N-acetylglucosamine residue linked to the Fc domain of the antibody.

15. The method of claim 1, wherein the antibody preparation comprises an N-linked glycan consisting of a single N-acetylglucosamine residue linked to Asn297 of the Fc domain of the antibody.

16. A method for manufacturing a fusion protein preparation, the method comprising:

culturing mammalian cells to produce a recombinant fusion protein preparation;

determining a level of an N-linked glycan consisting of a single N-acetylglucosamine residue in the produced preparation; and processing the fusion protein preparation as a pharmaceutical product based upon the determination.

17. The method of claim 16, further comprising comparing the determined level of N-linked glycans consisting of a single N-acetylglucosamine residue to a reference value for the fusion protein preparation for the level of N-linked glycans consisting of a single N-acetylglucosamine residue.

18. The method of claim 16, wherein the determining step comprises the use of a method for identifying or quantifying N-linked glycans consisting of a single N-acetylglucosamine residue selected from the group consisting of: chromatographic methods, mass spectrometry (MS) methods, electrophoretic methods, nuclear magnetic resonance (NMR) methods, monosaccharide analysis, fluorescence methods, UV-VIS absorbance, enzymatic methods, use of a detection molecule, and combinations thereof.

19. The method of claim 16, wherein the cells are cultured in a bioreactor.

20. The method of claim 16, wherein the processing step comprises disposing the fusion protein preparation into a container and the container is a gas or liquid tight container.

21. The method of claim 16, wherein the cells are CHO cells.

22. The method of claim 16, wherein the processing step comprises one or more of: formulating the fusion protein preparation; processing the fusion protein preparation into a drug product; combining the fusion protein preparation with a second component; lyophilizing the fusion protein preparation.

23. The method of claim 16, wherein the processing step comprises formulating the fusion protein preparation.

24. The method of claim 16, wherein the processing step comprises processing the fusion protein preparation into a drug product.

25. The method of claim 16, wherein the processing step comprises lyophilizing the fusion protein preparation.

26. The method of claim 16, wherein the processing step comprises one or more of: formulating the fusion protein preparation; processing the fusion protein preparation into a drug product; combining the fusion protein preparation with a second component; changing the concentration of the fusion protein in the preparation; lyophilizing the fusion protein preparation; combining a first and second aliquot of the fusion protein to provide a third, larger, aliquot; dividing the fusion protein preparation into smaller aliquots; disposing the fusion protein preparation into a container; packaging the fusion protein preparation; associating a container comprising the fusion protein preparation with a label; shipping or moving the fusion protein preparation to a different location.

27. The method of claim 16, wherein the fusion protein is a therapeutic fusion protein.

28. The method of claim 16, wherein the fusion protein preparation comprises an N-linked glycan consisting of a single N-acetylglucosamine residue.

29. The method of claim 16, wherein the fusion protein preparation comprises an N-linked glycan consisting of a single N-acetylglucosamine residue linked to an Fc domain of the fusion protein.

30. The method of claim 16, wherein the fusion protein preparation comprises an N-linked glycan consisting of a single N-acetylglucosamine residue linked to Asn297 of an Fc domain of the fusion protein.

31. The method of claim 1, comprising processing the antibody preparation as a pharmaceutical product if the level of N-linked glycan consisting of a single N-acetylglucosamine residue in the produced preparation is at least 0.5%.

32. The method of claim 1, comprising processing the antibody preparation as a pharmaceutical product if the level of N-linked glycan consisting of a single N-acetylglucosamine residue in the produced preparation is at least 1%.

33. The method of claim 16, comprising processing the fusion protein preparation as a pharmaceutical product if the level of N-linked glycan consisting of a single N-acetylglucosamine residue in the produced preparation is at least 0.5%.

34. The method of claim 16, comprising processing the fusion protein preparation as a pharmaceutical product if the level of N-linked glycan consisting of a single N-acetylglucosamine residue in the produced preparation is at least 1%.

\* \* \* \* \*

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asn-N-acetylhexosamine

<400> SEQUENCE: 1

Glu Glu Gln Tyr Asn Ser Thr Tyr Arg
1               5
```